US007491961B2

(12) United States Patent
Hakamata

(10) Patent No.: US 7,491,961 B2
(45) Date of Patent: Feb. 17, 2009

(54) SCANNING EXPOSURE APPARATUS, LINE LIGHT SOURCE, AND IMAGE INFORMATION READOUT SYSTEM

(75) Inventor: Kazuo Hakamata, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 390 days.

(21) Appl. No.: 11/017,669

(22) Filed: Dec. 22, 2004

(65) Prior Publication Data

US 2005/0133750 A1    Jun. 23, 2005

(30) Foreign Application Priority Data

Dec. 22, 2003  (JP)  ............................. 2003-423917
Dec. 22, 2003  (JP)  ............................. 2003-423918

(51) Int. Cl.
*G01N 23/04* (2006.01)
(52) U.S. Cl. .................. 250/591; 250/580; 250/581
(58) Field of Classification Search ................. 250/591, 250/580, 581
See application file for complete search history.

(56) References Cited

U.S. PATENT DOCUMENTS

| 3,665,246 | A | * | 5/1972 | Kurahashi et al. | ........ 315/169.3 |
| 4,535,468 | A | * | 8/1985 | Kempter | ..................... 378/31 |
| 4,922,100 | A | | 5/1990 | Takeuchi | |
| 5,336,978 | A | | 8/1994 | Alessio | |
| 6,268,614 | B1 | | 7/2001 | Imai | |
| 6,353,291 | B1 | | 3/2002 | Borgogno et al. | |
| 6,376,857 | B1 | | 4/2002 | Imai | |
| 6,614,045 | B2 | | 9/2003 | Shoji | |
| 6,642,650 | B1 | | 11/2003 | Struye et al. | |
| 6,878,957 | B2 | * | 4/2005 | Kuwabara | ................... 250/580 |
| 7,071,454 | B2 | * | 7/2006 | Iwakiri | .................... 250/208.1 |
| 2003/0057386 | A1 | | 3/2003 | Imai et al. | |
| 2005/0087708 | A1 | * | 4/2005 | Hakamata | ................... 250/591 |
| 2005/0098747 | A1 | * | 5/2005 | Yamaguchi | ................. 250/586 |
| 2005/0211933 | A1 | * | 9/2005 | Hakamata et al. | ........... 250/591 |
| 2006/0065865 | A1 | * | 3/2006 | Hakamata | ................... 250/591 |

* cited by examiner

*Primary Examiner*—Christine Sung
(74) *Attorney, Agent, or Firm*—Sughrue Mion, PLLC

(57) ABSTRACT

A panel light source includes: a planar light transmissive electrode formed by ITO film, which is 0.1 μm thick and 430 mm×430 mm in size; an EL layer; and a linear electrode layer formed by 4300 linear electrodes, which are arranged parallel in the Z direction. Each linear electrode is an aluminum electrode, which is 50 μm wide, 430 mm long, and 3 μm thick. The specific resistance of aluminum is $2.7 \times 10^{-6}$ Ω, and the resistance between first and second ends of the linear electrodes is 80 Ω. The specific resistance of ITO is $4 \times 10^{-4}$ Ω, and the resistance between a first and second end of the light transmissive electrode is 40 Ω. Negative drive voltage is applied to the first ends of the linear electrodes. Positive voltage is applied to the second end of the light transmissive electrode. Differences in voltage drops between the electrodes are reduced, compared to conventional line light sources.

15 Claims, 15 Drawing Sheets

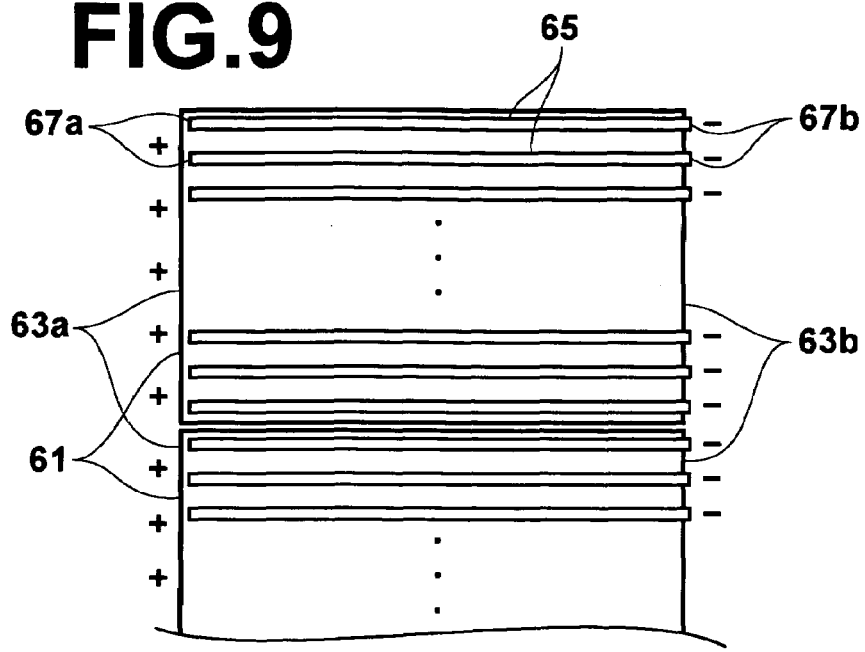
FIG.9
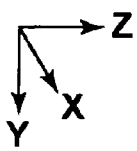
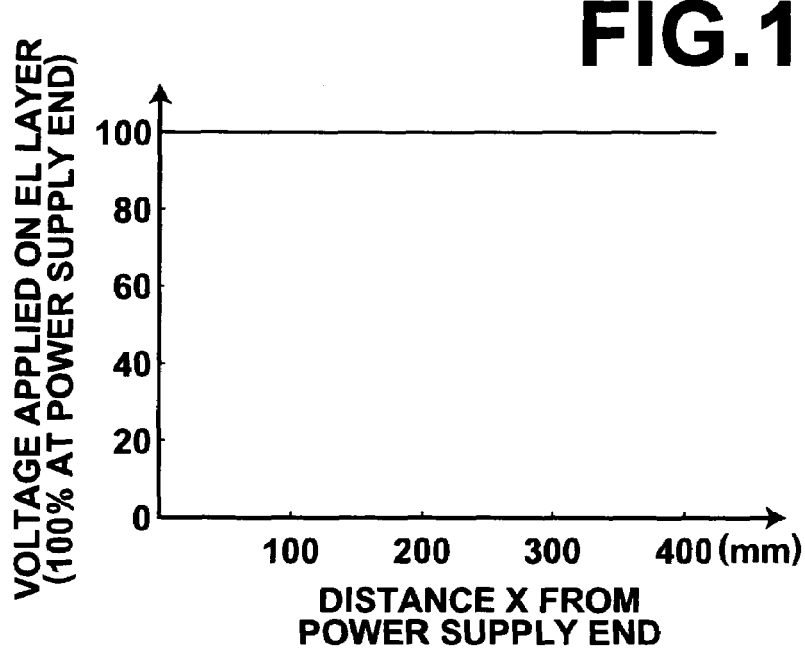
FIG.10

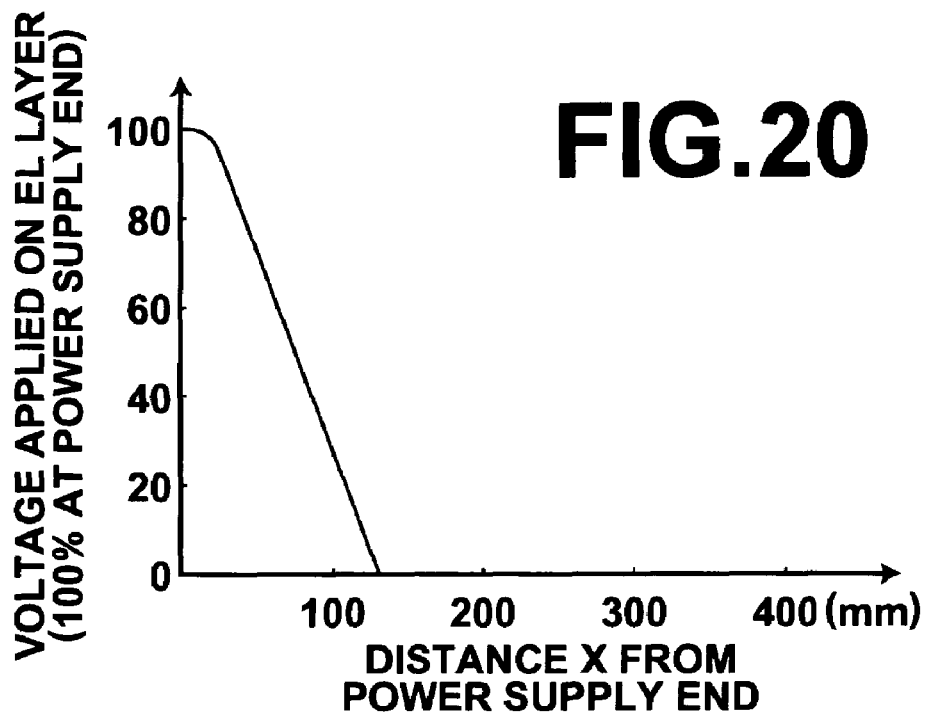
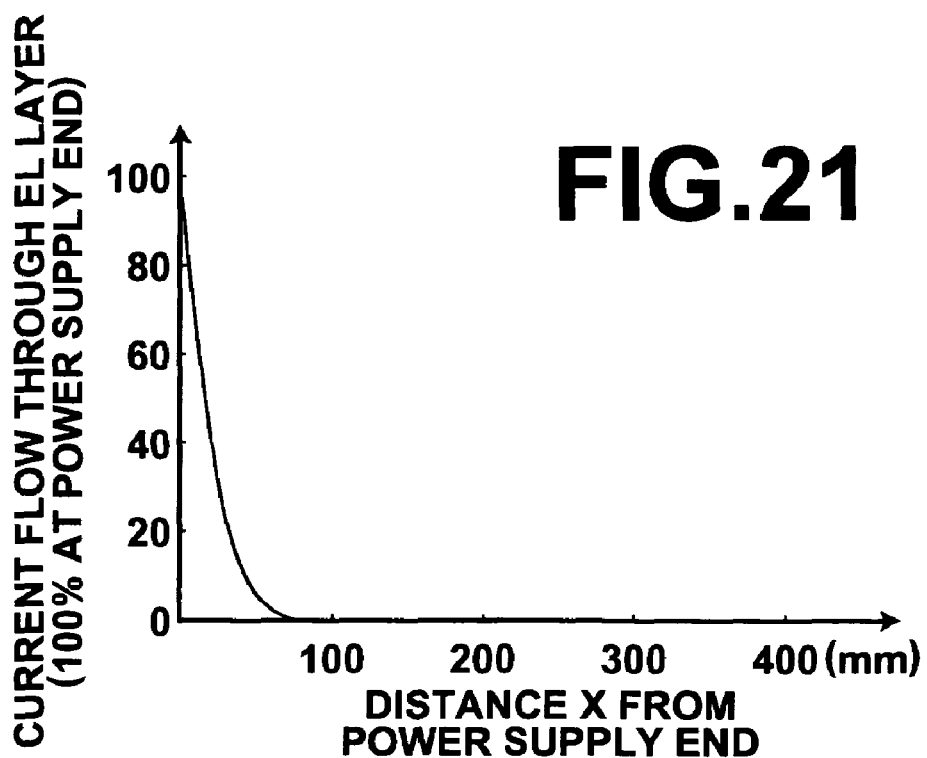

SCANNING EXPOSURE APPARATUS, LINE LIGHT SOURCE, AND IMAGE INFORMATION READOUT SYSTEM

BACKGROUND OF THE INVENTION

1. Field of the Invention

The present invention relates to a line light source, which is employed to irradiate readout light onto an image recording medium, to read out image information recorded thereon. Particularly, the present invention relates to a line light source that employs an EL layer, and to an image information readout system that employs such a light source.

The present invention also relates to a scanning exposure apparatus, which is employed to perform scanning exposure on an image recording medium, to read out image information recorded thereon. Particularly, the present invention relates to a scanning exposure apparatus that sequentially emits linear light beams from a panel light source, and performs scanning exposure in a scanning direction perpendicular to the longitudinal direction of the linear light beams. Further, the present invention relates to an image information readout system that employs such a scanning exposure apparatus.

2. Description of the Related Art

In the field of medical X-ray imaging, there are known image information readout systems, such as that disclosed in U.S. Pat. No. 6,268,614. This image information readout system employs an X-ray sensitive photoconductive material, such as a selenium plate formed of a-Se, as an electrostatic recording medium. Radiation, such as X-rays, bearing image information is irradiated onto the electrostatic recording medium, and latent image charges that bear the radiation image information are accumulated therein. An electrostatic latent image borne by the latent image charges is read out by scanning the electrostatic recording medium with linear light beams emitted from a line light source. The scanning causes electric current to be generated within the electrostatic recording medium. The electric current is detected via stripe electrodes. This configuration is adopted to reduce a radiation dose received by a subject, and also to improve diagnostic performance.

There are known other image information readout systems, as disclosed, for example, in U.S. Patent Application Publication No. 20030057386. This image information readout system employs stimulable phosphors as a recording medium. Stimulable phosphors store a portion of radiation energy irradiated thereon, and generate stimulated phosphorescence when scanned by linear light beams emitted from a line light source. Image information borne by the stimulable phosphors is read out by detecting the stimulated phosphorescence. Photodiodes, CCD's, or detectors having photoconductive layers that exhibit conductivity when irradiated with the stimulated phosphorescence may be employed as the detecting portion for detecting the stimulated phosphorescence. The detectors may either be in the form of a panel, or in linear form.

In the image information readout systems described above, scanning exposure apparatuses, in which line light sources are mechanically moved to perform scanning exposure with linear light beams, are employed. However, in the case that image information is read out employing such scanning exposure apparatuses, it is difficult to move the line light sources at high speed, therefore preventing acceleration of readout speed. For this reason, a scanning exposure apparatus has been proposed in U.S. Pat. No. 6,376,857.

This scanning exposure apparatus comprises a panel light source constituted by a great number of line light sources, which are arranged parallel at substantially equidistant intervals. Linear light beams are sequentially emitted by the panel light source at different timings, thereby performing scanning exposure. The panel light source comprises: light transmissive linear electrodes; a rear surface electrode constituted by a metal plate; and an EL layer provided between the linear electrodes and the rear surface electrode. Linear light beams are sequentially emitted, by causing electric current to flow through the EL layer between the linear electrodes and the rear surface electrode. ITO (Indium Tin Oxide) is utilized as the material of the light transmissive linear electrodes.

In scanning exposure apparatuses that employ light transmissive linear electrodes, an EL layer, and a planar metallic electrode as that described above, generally, the resolution during readout of image information from an image recording medium is inversely proportional to the gaps between the linear electrodes. Therefore, it is desirable that the line widths of the linear electrodes are narrow. Currently, development of scanning exposure apparatuses, in which linear electrodes have line widths on the order of several tens of μm is being anticipated. Meanwhile, it is desirable that the thickness of the light transmissive linear electrodes is thin, inorder to improve the light transmissivity therethrough. A thickness of 1 μm or less is preferable, and a thickness of 0.5 μm or less is further preferable. However, it is often the case that materials, which are capable of being formed into light transmissive linear electrodes, possess comparatively high specific resistances. For example, the specific resistance of ITO, which constitutes the light transmissive linear electrodes of the aforementioned scanning exposure apparatus, is approximately $4 \times 10^{-4}$ Ω. For this reason, in the case that the size of an image recording medium is 430 mm×430 mm, and the linear electrodes have line widths of 50 μm, thicknesses of 1 μm, and lengths of 430 mm, the resistance in the longitudinal direction thereof may be obtained as follows. First, the sheet resistance of ITO having a thickness of 1 μm is:

$$4 \times 10^{-4} \text{ Ω·cm}/1 \times 10^{-4} \text{ cm} = 4 \text{ Ω/sq}$$

Accordingly, the resistance of the linear electrodes in the longitudinal direction thereof may be calculated by substituting the above value in an equation (sheet resistance×length)/line width, to yield:

$$(4 \text{ Ω/sq} \times 430 \text{ mm})/(50 \times 10^{-3} \text{ mm}) \approx 34 \text{ KΩ}$$

If an electric current of 2 mA is caused to flow through the linear electrodes, a potential difference of 68V is generated at the two ends thereof. There is a problem that the amount of light generated in the EL layer at the ends of the linear electrodes, to which drive current is not connected, is significantly reduced, due to a voltage drop. In the case that the thickness of ITO is made as thin as 0.4 μm in order to improve the light transmissive property thereof, the resistance of the linear electrodes formed thereby will be approximately 86 KΩ. FIG. 20 is a graph that illustrates the relationship between the distance x from an end of a linear electrode, to which voltage is applied, and a voltage V(x), which is applied to an EL layer. The graph assumes that an planar aluminum electrode (specific resistance: $2.7 \times 10^{-6}$ Ω·cm) having a thickness of 0.1 μm is employed as a rear surface electrode, and that a voltage of 65V is applied to one end of the linear electrode. As can be seen from FIG. 20, the voltage drops to approximately 20% at a portion about 100 mm distant from the end of the linear electrode. FIG. 21 is a graph that illustrates the relationship between the distance x from an end of a linear electrode and the amount of electric current D(x), which flows through an EL layer. It can be seen from this graph that hardly any electric current flows through the EL layer at a portion 100 mm distant from the end of the linear electrode. For this reason, the EL layer does not emit light at a portion 100 mm distant from the end of the linear electrode. That is, in a scanning exposure apparatus configured as described above, it is difficult to cause an EL layer to emit light at the end of an electrode, to which drive current is not connected.

SUMMARY OF THE INVENTION

The present invention has been developed in view of the points above. It is an object of the present invention to provide a scanning exposure apparatus comprising a panel light source, which employs an EL layer that is capable of emitting linear light beams with improved light emitting properties in the longitudinal direction thereof. It is also an object of the present invention to provide an image information readout system that employs such a scanning exposure apparatus.

It is another object of the present invention to provide a line light source, which is capable of emitting linear light beams with little fluctuation in light emission in the longitudinal direction thereof, even when driven at low voltage. It is also an object of the present invention to provide an image information readout system that employs such a line light source.

The scanning exposure apparatus according to the present invention comprises:

a panel light source for sequentially emitting linear light beams; and an exposure control means for controlling the emission of light by the panel light source, wherein:

the panel light source comprises:

at least one planar light transmissive electrode;

a plurality of linear electrodes, which are arranged in a first direction; and an EL layer, provided between the light transmissive electrode and the linear electrodes;

the exposure control means causes electric current to flow through the linear electrodes in a sequential manner, thereby causing electric current to flow in the EL layer provided between the linear electrodes and the light transmissive planar electrode, to cause sequential emission of the linear light beams; and scanning exposure is performed in the first direction, which is perpendicular to the longitudinal direction of the linear light beams.

Note that the "planar light transmissive electrode" refers to a light transmissive electrode having an area corresponding to at least two opposing linear electrodes. A single light transmissive electrode or a plurality of light transmissive electrodes may be provided.

The resistance of the light transmissive electrode and the resistance of the linear electrodes may be substantially equal. Note that here, the "resistance of the linear electrodes" refers to the resistance in the longitudinal direction of the linear electrodes. Meanwhile, the "resistance of the light transmissive electrode" refers to the resistance between portions that correspond to the ends of the linear electrodes in the longitudinal direction thereof. The phrase "substantially equal" means that the ratio, of the resistance of the linear electrodes with respect to the resistance of the light transmissive electrode, is 0.5 or greater and 2 or less.

A configuration may be adopted, wherein:

the linear electrodes are formed by thin films having a sheet resistance ra, and which are arranged at a pitch P;

the at least one light transmissive electrode is formed by a plurality of rectangular thin films having a sheet resistance rc, which are arranged in the first direction at substantially equidistant gaps having a width wi; and the width wc of the light transmissive electrode satisfies the equation:

$wc \geq n \cdot P - wi$, wherein n is the maximum integer that satisfies the equation:

$$n < \frac{wa \cdot rc}{ra \cdot P}.$$

Further, the width wc may satisfy the equation:

$wc \leq (n+1) \cdot P + wa$.

The first image information readout system according to the present invention comprises:

an image recording medium, on which image information has been recorded; and a scanning exposure apparatus for performing scanning exposure, employing linear light beams as readout light, on the image recording medium, in a scanning direction perpendicular to the longitudinal direction of the linear light beams; wherein:

the scanning exposure apparatus comprises:

a panel light source comprising:

at least one planar light transmissive electrode;

a plurality of linear electrodes, which are arranged in a first direction; and an EL layer, provided between the light transmissive electrode and the linear electrodes; and an exposure control means for causing electric current to flow through the linear electrodes in a sequential manner, thereby causing electric current to flow in the EL layer provided between the linear electrodes and the light transmissive planar electrode, to cause sequential emission of the linear light beams.

A line light source according to the present invention comprises:

linear electrodes;

opposing electrodes corresponding to the linear electrodes; and an EL layer provided between the linear electrodes and the opposing electrodes; wherein:

either one of the linear electrodes and the opposing electrodes are light transmissive;

linear light beams are emitted by applying a drive voltage to a first end of the linear electrodes, causing electric current to flow between the linear electrodes and the opposing electrodes through the EL layer;

a voltage different from the drive voltage is applied to the opposing electrodes at a portion facing a second end of the linear electrodes, to which the drive voltage is not applied; and the ratio of the resistance between the two ends of the linear electrodes with respect to the resistance between the portions of the opposing electrodes corresponding to the two ends of the linear electrodes is 0.5 or greater and 2 or less.

Note that "a voltage different from the drive voltage is applied . . . " includes cases in which 0 voltage is applied, that is, when the opposing electrodes are grounded.

The ratio may be 0.9 or greater and 1.1 or less. Alternatively, the ratio may be 1.

A configuration may be adopted, wherein:

if the linear electrodes are formed by thin films having a sheet resistance ra, widths wa, and lengths L, the resistance of the linear electrodes is expressed as $$\frac{ra \cdot L}{wa};$$

and if the opposing electrodes are formed as rectangles by thin films having a sheet resistance rc, widths wc, and lengths L, the resistance of the opposing electrodes is expressed as $$\frac{rc \cdot L}{wc}.$$

The second image information readout system according to the present invention comprises:

an image recording medium, on which image information has been recorded;

an exposure head, in which a plurality of line light sources for emitting readout light are arranged; and a scanning exposure control portion for causing the readout light to be emitted by the line light sources at different timings, during readout of the image information; wherein:

the line light source comprises:

linear electrodes;

opposing electrodes corresponding to the linear electrodes; and an EL layer provided between the linear electrodes and the opposing electrodes;

either one of the linear electrodes and the opposing electrodes are light transmissive;

linear light beams are emitted by applying a drive voltage to a first end of the linear electrodes, causing electric current to flow between the linear electrodes and the opposing electrodes through the EL layer;

a voltage different from the drive voltage is applied to the opposing electrodes at a portion facing a second end of the linear electrodes, to which the drive voltage is not applied; and the ratio of the resistance between the two ends of the linear electrodes with respect to and the resistance between the portions of the opposing electrodes corresponding to the two ends of the linear electrodes is 0.5 or greater and 2 or less.

Note that both of the linear electrodes and the opposing electrodes may be light transmissive. In this case, it does not matter which side of the line light source faces the image recording medium. However, in the case that only one of the two types of electrodes are light transmissive, the side of the line light source toward the light transmissive electrodes must face the image recording medium.

The image recording medium may be an electrostatic recording medium that records image information as an electrostatic latent image, and generates electric current corresponding to the electrostatic latent image when subjected to scanning exposure by the readout light. Alternatively, the image recording medium may be a stimulable phosphor recording medium that accumulatively records image information, and emits stimulated phosphorescence corresponding to the image information when subjected to scanning exposure by the readout light.

The scanning exposure apparatus of the present invention comprises the panel light source constituted by the planar light transmissive electrode, the plurality of linear electrodes, which are arranged in the first direction, and the EL layer provided between the light transmissive electrode and the linear electrodes. Linear light beams are caused to be sequentially emitted by sequentially causing electric current to flow through the linear electrodes. Therefore, the linear electrodes need not be light transmissive themselves. Accordingly, materials having low resistance, such as metal, may be used to form the linear electrodes. Thus, the resistance of the linear electrodes decreases, voltage drops in the longitudinal direction thereof are reduced, and emission of linear light beams having good light emission properties in the longitudinal direction is enabled.

The resistance of the light transmissive electrode and the resistance of the linear electrodes may be substantially equal. In this case, voltage drops within the light transmissive electrode and the linear electrodes will become substantially equal. Therefore, the potential differences between the light transmissive electrodes and the linear electrodes become substantially equal at all positions along the longitudinal direction of the linear light beams. Accordingly, emission of linear light beams, which have little fluctuation in light emission in the longitudinal direction thereof, is enabled.

A configuration may be adopted, wherein:

the linear electrodes are formed by thin films having a sheet resistance ra, and which are arranged at a pitch P;

the at least one light transmissive electrode is formed by a plurality of rectangular thin films having a sheet resistance rc, which are arranged in the first direction at substantially equidistant gaps having a width wi; and the width wc of the light transmissive electrode satisfies the equation:

wc $\geq$ n·P−wi, wherein n is the maximum integer that satisfies the equation:

$$n < \frac{wa \cdot rc}{ra \cdot P}.$$

In this case, the resistance of the light transmissive electrode is less than or equal to a value approximating the resistance of the linear electrodes, which is greater than or equal to the resistance of the linear electrodes. Therefore, voltage drops in the light transmissive electrode can also be suppressed, thereby enabling emission of linear light beams having improved light emission properties.

The width wc may further satisfy the equation:

wc $\leq$ (n+1)·P+wa.

In this case, the resistance of the light transmissive electrode is less than or equal to a value approximating the resistance of the linear electrodes, which is greater than or equal to the resistance of the linear electrodes. At the same time, the resistance of the light transmissive electrode is greater than or equal to a value approximating the resistance of the linear electrodes, which is less than or equal to the resistance of the linear electrodes. Therefore, voltage drops within the linear electrodes and voltage drops within the light transmissive electrode partially cancel each other out. Accordingly, emission of linear light beams, having reduced fluctuations in light emission, is enabled.

Note that the theoretically ideal line width wc of the light transmissive electrode is:

$$wc = \frac{rc \cdot wa}{ra}.$$

In this case, the resistance of the linear electrodes and the resistance of the light transmissive electrodes become equal. Therefore, voltage drops within the linear electrodes and voltage drops within the light transmissive electrode cancel each other out. Accordingly, emission of linear light beams, having substantially suppressed fluctuations in light emission, would be enabled. However, if a gap between light transmissive electrodes is at a position that corresponds to an opposing linear electrode, electrical current, which is different from that which flows through other linear electrodes, flows through that linear electrode. This would be a factor in generating fluctuations in light emission properties among the linear electrodes. For this reason, it is desirable that the width wc of the light transmissive electrode be set such that gaps are not formed at positions corresponding to opposing linear electrodes. In addition, the width wi of the gaps must satisfy the condition: $wi \leq P-wa$. Considering these conditions, the most appropriate widths wc' of the light transmissive electrode may be derived on a case by case basis, as shown below.

Assuming that $$\frac{rc \cdot wa}{ra} = A:$$

In the case that $$A < n \cdot P + \frac{wa - wi}{2},$$

$wc' = n \cdot P - wi$.

In the case that $$n \cdot P + \frac{wa - wi}{2} \leq A < n \cdot P + wa,$$

$wc' = n \cdot P + wa$.

In the case that $n \cdot P + wa \leq A < (n+1) \cdot P - wi$, $$wc' = A = \frac{rc \cdot wa}{ra}.$$

In the case that $$(n+1) \cdot P - wi \leq A < (n+1) \cdot P + \frac{wa - wi}{2},$$

$wc' = (n+1) \cdot P - wi$

In the case that $$A \geq (n+1) \cdot P + \frac{wa - wi}{2},$$

$wc' = (n+1) \cdot P + wa$.

The width wc is determined as described above. Thereby, the light transmissive electrodes are provided such that gaps therebetween are not at positions that oppose linear electrodes. Accordingly, all of the linear electrodes emit light in the same manner, while at the same time, linear light beams having minimal fluctuations in light emission within each of the linear electrodes are obtained.

The first image information readout system of the present invention comprises the scanning exposure apparatus, which is equipped with the panel light source and the scanning exposure control portion. The panel light source comprises: the planar light transmissive electrode; the linear electrodes, which are arranged in the scanning direction; and the EL layer, which is provided between the light transmissive electrode and the linear electrodes. The scanning exposure control portion causes electric current to flow through the linear electrodes in a sequential manner, thereby causing electric current to flow in the EL layer provided between the linear electrodes and the light transmissive planar electrode, to cause sequential emission of the linear light beams. Therefore, image information is read out by readout light, which are linear light beams having improved light emission properties in the longitudinal direction thereof. Accordingly, the reliability of the readout image information is improved.

In the line light source of the present invention, a voltage different from the drive voltage is applied to the opposing electrodes at the portion facing the second end of the linear electrodes, to which the drive voltage is not applied. Therefore, voltage drops that occur in the linear electrodes and the voltage drops that occur in the opposing electrodes cancel each other out. In addition, the ratio of the resistance between the two ends of the linear electrodes with respect to the resistance between the portions of the opposing electrodes corresponding to the two ends of the linear electrodes is 0.5 or greater and 2 or less. Accordingly, the ratio of the voltage drops that occur in the linear electrodes with respect to the voltage drops that occur in the opposing electrodes is also 0.5 or greater and 2 or less. Thereby, differences between the voltage drops that occur in the linear electrodes and the voltage drops that occur in the opposing electrodes are reduced. Therefore, the potential differences between the light transmissive electrodes and the linear electrodes are reduced at all positions along the longitudinal direction of the linear light beams. Thus, emission of linear light beams, which have little fluctuation in light emission in the longitudinal direction thereof, is enabled, even if driven with low voltage.

In the case that the above ratio is 0.9 or greater and 1.1 or less, the voltage drops that occur in the linear electrodes and the voltage drops that occur in the opposing electrodes become substantially equal. Therefore, the potential differences between the linear electrodes and the opposing electrodes become substantially equal at all positions along the longitudinal direction of the linear light beams. Accordingly, emission of linear light beams, which have further reduced fluctuation in light emission in the longitudinal direction thereof, is enabled, even if driven with low voltage.

In the case that the above ratio is 1, the voltage drops that occur in the linear electrodes and the voltage drops that occur in the opposing electrodes become equal. Therefore, the potential differences between the light transmissive electrodes and the linear electrodes become equal at all positions along the longitudinal direction of the linear light beams. Accordingly, emission of linear light beams, which have uniform fluctuation in light emission in the longitudinal direction thereof, is enabled.

A configuration may be adopted, wherein:

if the linear electrodes are formed by thin films having a sheet resistance ra, widths wa, and lengths L, the resistance of the linear electrodes is expressed as $$\frac{ra \cdot L}{wa}; \text{ and}$$

if the opposing electrodes are formed as rectangles by thin films having a sheet resistance rc, widths wc, and lengths L, the resistance of the opposing electrodes is expressed as $$\frac{rc \cdot L}{wc}.$$

In this case, the resistances of the electrodes can be easily compared.

The second image information readout system of the present invention comprises the line light source, which is constituted by:

linear electrodes;

opposing electrodes corresponding to the linear electrodes; and an EL layer provided between the linear electrodes and the opposing electrodes; wherein either one of the linear electrodes and the opposing electrodes are light transmissive;

linear light beams are emitted by applying a drive voltage to a first end of the linear electrodes, causing electric current to flow between the linear electrodes and the opposing electrodes through the EL layer;

a voltage different from the drive voltage is applied to the opposing electrodes at a portion facing a second end of the linear electrodes, to which the drive voltage is not applied; and the ratio of the resistance between the two ends of the linear electrodes with respect to and the resistance between the portions of the opposing electrodes corresponding to the two ends of the linear electrodes is 0.5 or greater and 2 or less. Therefore, the potential differences between the linear electrodes and the opposing electrodes are reduced. Accordingly, emission of linear light beams, which have little fluctuation in light emission in the longitudinal direction thereof, is enabled, even if driven with low voltage. Thus, image information is enabled to be read out accurately.

BRIEF DESCRIPTION OF THE DRAWINGS

FIG. 9 is a model diagram that illustrates the relationship between light transmissive electrodes and linear electrodes.

FIG. 10 is a graph that illustrates the relationship between the distance from a power supply end of a linear electrode and a voltage, which is applied to an EL layer.

FIG. 20 is a graph that illustrates the relationship between the distance from the power supply end and electric current that flows through the EL layer.

FIG. 21 is a graph that illustrates the relationship between the distance from the power supply end and electric current that flows through the EL layer.

DESCRIPTION OF THE PREFERRED EMBODIMENTS

Figure 1:
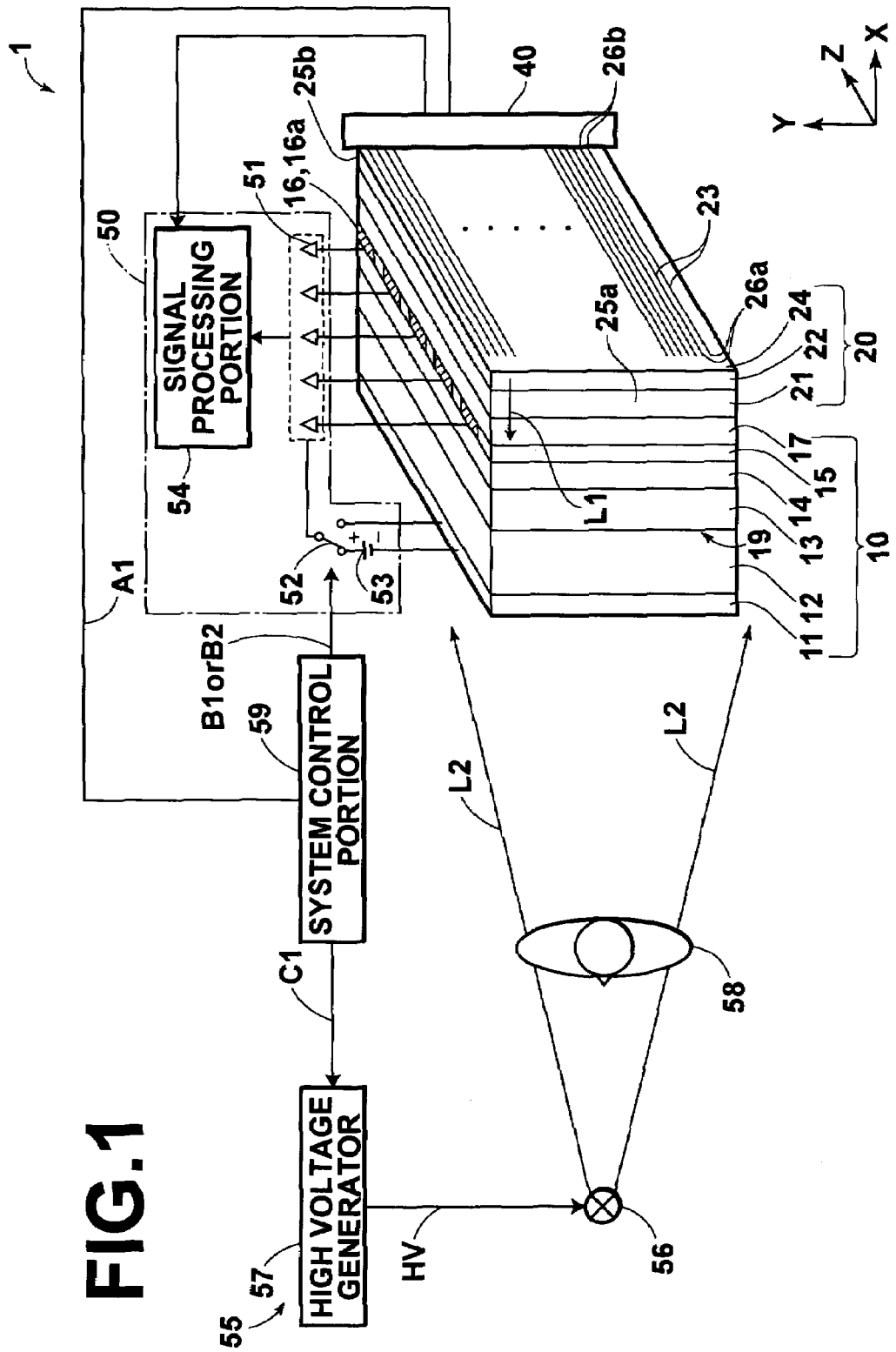
FIG. 1 is a schematic structural diagram that illustrates an image information recording/readout system according to a first embodiment of the present invention.

Hereinafter, embodiments of the present invention will be described with reference to the attached drawings. FIG. 1 is a schematic structural diagram that illustrates an image information recording/readout system 1 according to a first embodiment of the present invention, in which a readout scanning exposure apparatus of the present invention is employed.

As illustrated in FIG. 1, the image information recording/readout system 1 comprises: an image recording medium 10, which is capable of recording electrostatic latent images and is of a size 430 mm×430 mm; a panel light source 20, for scanning and exposing the image recording medium 10 with readout light L1; a scanning exposure control portion 40, for controlling the operation of the panel light source 20; a readout portion 50, for reading out the image information recorded on the image recording medium; a radiation emitting portion 55, for irradiating radiation L2, which is a recording light; and a system control portion 59, for controlling the scanning exposure control portion 40, the readout portion 50, and the radiation emitting portion 55.

The image recording medium 10 operates in the following manner. When radiation L2 (X-rays, for example), which has passed through a subject and bears image information, is irradiated on a first electrode layer 11 (conductive layer), charges are generated within a recording light photoconductive layer 12. The charges generated within the recording light photoconductive layer 12 are accumulated as latent image charges at a charge accumulating portion 19, which is at the interface of the recording light photoconductive layer 12 and a charge transport layer 13. When a second electrode layer 15 (conductive layer) is scanned with the readout light L1, charges are generated within a readout light photoconductive layer 14. The charges generated within the readout light photoconductive layer 14 couple with the latent image charges, and generate electric current corresponding to the amount of latent image charges. Note that a transparent insulative layer 17, which is transmissive with respect to the readout light L1, is provided on the exterior side of the second electrode layer 15.

The second electrode layer 15 is constituted by a great number of linear electrodes (the hatched portion in FIG. 1), which are arranged as stripes. Hereinafter, the electrodes of the second electrode layer 15 will be referred to as stripe electrodes 16, and individual linear electrodes will be referred to as elements 16a. Amorphous materials having a-Se as a main component are utilized for the recording light photoconductive layer 12, the chare transport layer 13, and the readout light photoconductive layer 14. Note that as indicated in FIG. 1, the stacking direction of the recording light photoconductive layer 12, the charge transport layer 13, the readout light photoconductive layer 14, the second electrode layer 15, and the insulative layer 17 is designated as the X direction. The longitudinal direction of the stripe electrodes 16 is designated as the Y direction. The direction which is perpendicular to the XY plane is designated as the Z direction.

Figure 2:
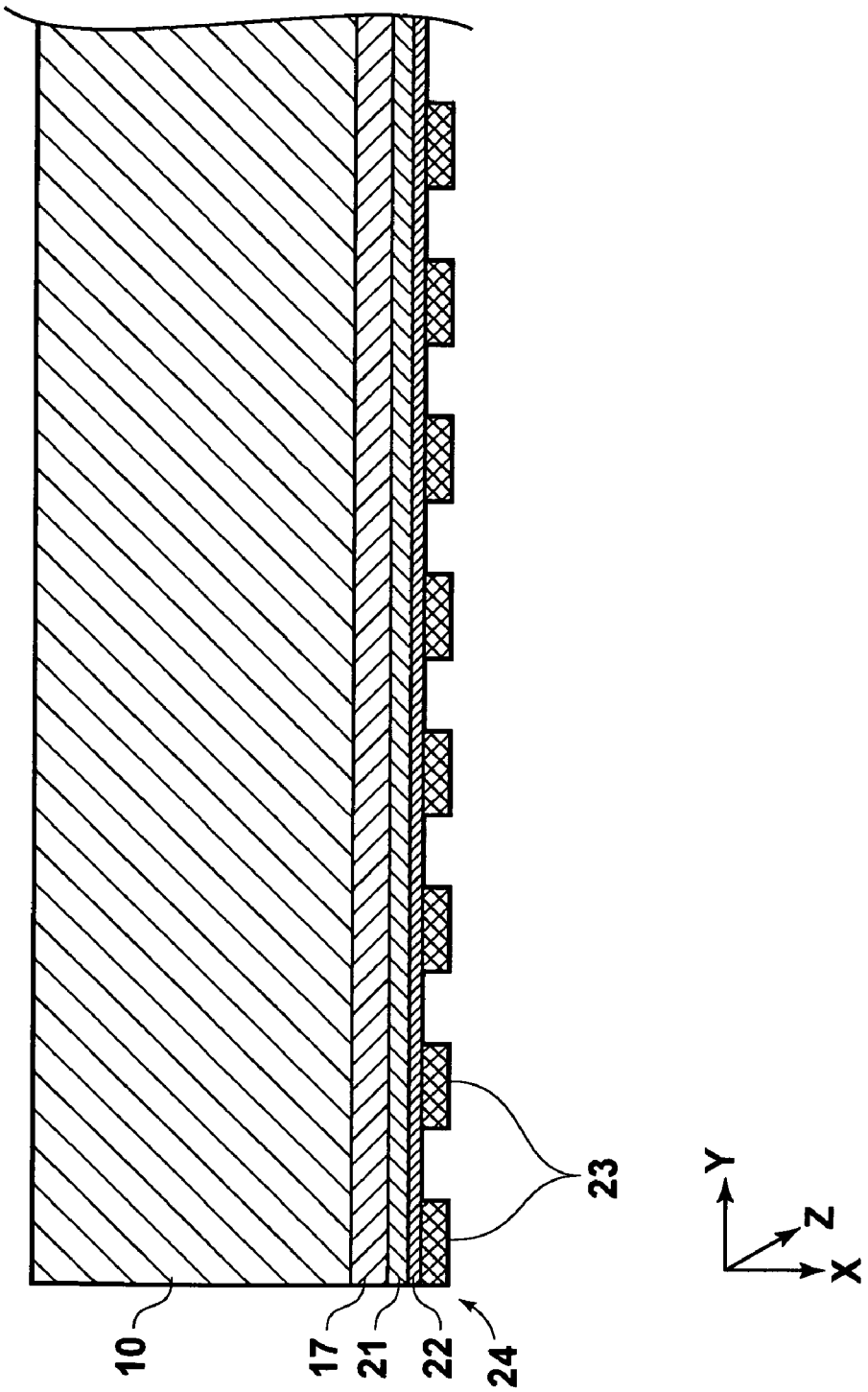
FIG. 2 is a partial sectional view of a panel light source.

FIG. 2 is a partial sectional view of the panel light source 20, taken along the XY plane. The panel light source 20 comprises: a planar light transmissive electrode 21 formed by an ITO film, having a thickness of 0.1 μm and a size of 430 mm×430 mm; an EL layer 22, having a thickness of 0.1 μm and a size of 430 mm×430 mm; and a linear electrode layer 24 formed by 4300 linear electrodes 23, which are arranged parallel with substantially equidistant gaps therebetween in the Z direction. Each linear electrode 23 is an aluminum electrode having a width of 50 μm, a length of 430 mm, and a thickness of 0.1 μm. The linear electrodes 23 are arranged with 100 μm gaps therebetween. As illustrated in FIG. 2, the planar light transmissive electrode 21 is provided in contact with the insulative layer 17, to correspond in position to the image recording medium 10. The light transmissive electrode 21, the EL layer 22, and the linear electrode layer 24 are stacked in this order in the X direction. The EL layer 22 is an organic EL layer. Alternatively, an inorganic EL layer may be employed. The light transmissive electrode 21 has ends 25a and 25b, in the Z direction. Of the ends 25a and 25b, the end 25a is grounded. Each of the linear electrodes 23 has ends 26a and 26b in the Z direction. Of the ends 26a and 26b, the ends 26b, which are at the opposite end of the linear electrodes 23 from the end 25a of the light transmissive electrode 21, are connected to the scanning exposure control portion 40.

Note that the specific resistance of aluminum is $2.7 \times 10^{-6}$ Ω·cm, and the resistance between the end 26a and the end 26b of each of the linear electrodes 23 is 2.3 KΩ. For this reason, in the case that a 2 mA current flows through the linear electrode 23, the voltage drop between the end 26a and the end 26b is 4.6V.

The scanning exposure control portion 40 sequentially applies a predetermined DC voltage to the ends of each of the linear electrodes 23, when a control signal A1, commanding that readout scanning be performed, is input thereto. Thereby, the readout light L1 is sequentially emitted from the panel light source 20 at different timings.

The readout portion 50 comprises a great number of current detecting amplifiers 51, each of which is connected to an inverting input terminal for each element 16a of the stripe electrodes 15. The first electrode layer 11 of the image recording medium 10 is connected to one of the inputs of a switch 52 and the negative pole of a power source 53. The positive pole of the power source 53 is connected to the other input of the switch 52. The output of the switch 52 is commonly connected to non-inverting input terminals of operating amplifiers (not shown) that constitute each of the current detecting amplifiers 51.

During readout scanning, electric current flows through each of the elements 16a when the side of the image recording medium 10 toward the stripe electrode 16 is irradiated (subjected to scanning exposure) by the readout light L1. Each of the current detecting amplifiers 51 simultaneously detects (parallel detection) the electric current that flows through the element 16a that it is connected to. The detection results are output to a signal processing portion 54. Data regarding the exposure position, which has been subjected to exposure by the readout light L1, is sequentially input from the scanning exposure control portion 40 to the signal processing portion 54. The exposure position data and the detection results, which have been input from the current detecting amplifiers 41, are combined and recorded in the signal processing portion 54. After readout scanning is complete, image information corresponding to a single image is generated, based on the detection results and the exposure position data.

Note that the details of the construction of the current detection amplifiers 51 are not related to the substance of the present invention. Therefore, a detailed description thereof will be omitted here. However, various well known constructions may be adopted. It goes without saying that the manner of connections among the power source 53, the switch 52, and each of the elements 16a will differ, depending on the construction of the current detecting amplifiers 51. Note that in the present embodiment, the switch 52 is switched over to the power source 53 when a control signal B1, commanding that image recording be performed, is input, and switched over tot the first electrode layer 11 when a control signal B2, commanding that readout be performed, is input.

The radiation emitting portion 55 comprises: a radiation source 56, for generating radiation L2; and a high voltage generator 57, for generating electricity to drive the radiation source 56.

The high voltage generator 57 supplies high voltage HV to the radiation source 56 when a control signal C1, commanding that radiation L2 be emitted, is input, to cause the radiation source 56 to emit radiation L2 for a predetermined amount of time.

Note that the system control portion 59 outputs: the control signal A1, commanding that scanning exposure be performed, to the scanning exposure control portion 40; the control signal B1, commanding that recording of image information be performed, or the control signal B2, commanding that readout of image information be performed, to the switch 52; and the control signal C1, commanding that radiation L2 be emitted, to the high voltage generator 57.

Hereinafter, the operation of the image information recording/readout system having the above construction will be described. First, an electrostatic latent image is recorded onto the image recording medium 10. A recording voltage is applied between the electrodes of the first electrode layer 11 and the strip electrodes 16. In this state, the first electrode layer 11 is irradiated with recording radiation L2, to record the electrostatic latent image onto the image recording medium 10. Specifically, first, the system control portion 59 outputs the control signal B1 to the switch 52. This is done to enable charges generated within the recording photoconductive layer 12 to be accumulated at the charge accumulating portion 19. When the control signal B1 is input, the switch switches over to the power source 53. The power source applies a DC voltage of a predetermined size between the electrodes of the first electrode layer 11 and the strip electrodes 16 as a recording voltage. Thereby, the electrodes of the first electrode layer 11 and the strip electrodes 16 become charged.

After the application of the recording voltage, the system control portion 59 outputs the control signal C1 to the high voltage generator 57. This causes the high voltage generator 57 to supply high voltage HV to the radiation source 56, and radiation L2 is emitted therefrom. The radiation L2 is irradiated onto a subject 58. Radiation L2, which has passed through the subject 58 and therefore bears image information, is irradiated onto the image recording medium 10 for a set irradiation time. Due to this irradiation, positive and negative charge pairs are generated within the recording light photoconductive layer 12 of the image recording medium. Negative charges of the charge pairs become concentrated at the elements 16a of the stripe electrodes along a predetermined electric field distribution, and are accumulated as latent image charges at the charge accumulating portion 19, which is the interface between the recording light photoconductive layer 12 and the charge transport layer 13. The amount of latent image charges is substantially proportional to the irradiated radiation dosage. Therefore, the latent image charges bear an electrostatic latent image of the subject 58. Meanwhile, positive charges of the charge pairs are drawn toward the first electrode layer 11, where they couple with negative charges, which are supplied by the power source 53, and disappear.

Next, the electrostatic latent image is read out from the image recording medium 10. The system control portion 59 outputs the control signal B2 to the switch 52, to cause the electrodes of the first electrode layer 11 and the stripe electrodes 16 to be at the same electric potential. Next, the control signal A1 is output to the scanning exposure control portion 40. The scanning exposure control portion 40 applies DC voltage to the topmost linear electrode 23, as illustrated in FIG. 1. Thereby, electric current flows in the EL layer 22, which is between the linear electrodes 23 and the light transmissive electrode 21, and the EL layer 22 is caused to emit a linear light beam. The linear light beam, emitted by the EL layer 22, is irradiated onto the image recording medium 10, as readout light L1. Thereafter, DC voltage is sequentially applied to adjacent linear electrodes 23, to emit readout light L1. Scanning exposure of the image recording medium 10 is complete after DC voltage is applied to the lowermost linear electrode 23, and readout light L1 is emitted at the portion of the EL layer 22 corresponding thereto.

Positive and negative charge pairs are generated within the readout light photoconductive layer 14 at positions that correspond to the scanning positions scanned and irradiated by the readout light L1. Positive charges of the charge pairs are drawn toward the negative charges (latent image charges), which are accumulated at the charge accumulating portion 16, at high speed, couple with the latent image charges, and disappear. Meanwhile, the negative charges of the charge pairs couple with positive charges, which are supplied to the strip electrodes 16 by the power source 53, and disappear. In this manner, the negative charges, which are accumulated at the charge accumulating portion 19 disappear due to charge coupling. Electric current, caused by the movement of charges during the charge coupling, is generated within the image recording medium 10. The electric current is simultaneously detected by the current detecting amplifiers 51, which are connected to each element 16a, and the detection results are output to the signal processing portion 54.

The electric current that flows through the image recording medium 10 during readout corresponds to the latent image charges, that is, the electrostatic latent image. Therefore, the electrostatic latent image can be read out, that is, image signals that correspond to the electrostatic latent image can be obtained, by detecting the electric current. Note that the detection by the current detecting amplifiers 51 is performed synchronously with the switching timing of the emission position of the readout light L1. That is, the detection by the current detecting amplifiers 51 is performed synchronously with the switching timing of the linear electrodes 23, and image signals corresponding to 4300 lines are obtained.

After scanning exposure is complete, the signal processing portion 54 generates image information corresponding to a single image, based on the detection results (image signals).

As is clear from the above description, the panel light source 20 of the present embodiment comprises: the planar light transmissive electrode 21 formed with ITO; the 4300 linear electrodes 23, which are arranged in the Z direction; and the EL layer 22 provided between the light transmissive electrode 21 and the linear electrodes 23. Therefore, the linear electrodes 23 need not be light transmissive themselves. Accordingly, materials having low resistance, such as metal, may be used to form the linear electrodes 23. Thus, the resistance of the linear electrodes 23 decreases, voltage drops in the longitudinal direction thereof are reduced, and emission of readout light L1 having good light emission properties in the longitudinal direction is enabled. Note that the width of the linear electrodes 23 is 50 µm, and the thicknesses of the light transmissive electrode 21 and the EL layer 22 are both 0.1 µm. Therefore, there is hardly any difference in the line width of emitted light, even if metallic electrodes are utilized as the linear electrodes instead of the conventional light transmissive linear electrodes. In the case that readout light L1 having a narrower line width is desired, a multilayered dielectric film layer may be provided on the electrodes to form dielectric mirrors as optical resonator structures, and the beam spread of the readout light L1 may be improved.

Figure 3:
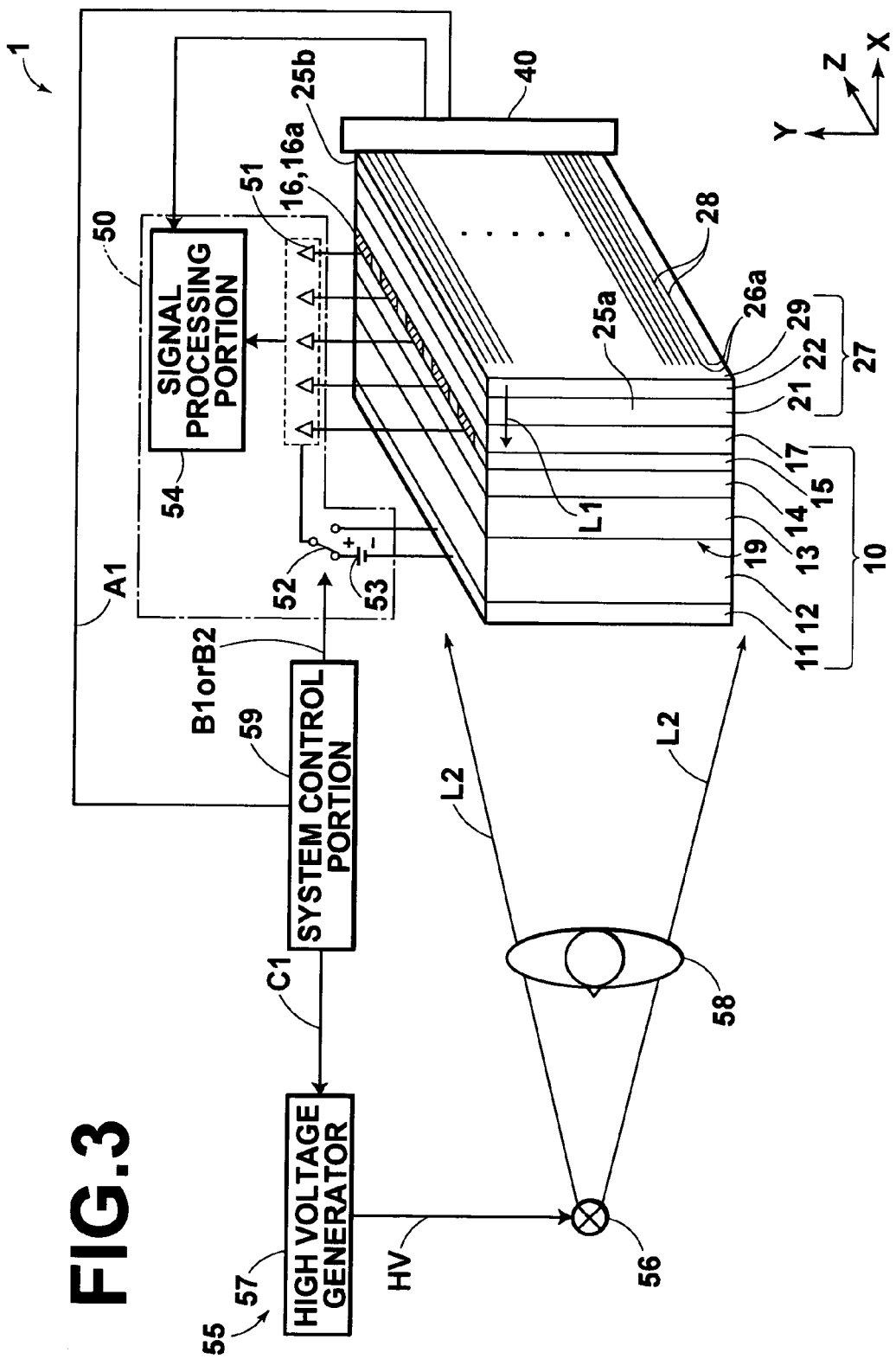
FIG. 3 illustrates a modification of the image information recording/readout system according to the first embodiment.

FIG. 3 illustrates a modification of the present embodiment. In this modification, a panel light source 27 is employed instead of the panel light source 20. The panel light source 27 comprises: the light transmissive electrode 21; the EL layer 22; and 4300 aluminum electrodes having a width of 50 µm and a thickness of 1 µm as linear electrodes 32. The linear electrodes 32 are arranged parallel to each other in the Z direction. The specific resistance of aluminum is $2.7 \times 10^{-6}$ Ω·cm, therefore the resistance between the two ends of the linear electrodes 32 in the Z direction becomes 232 Ω. For this reason, if an electric current of 2 mA flows through the linear electrodes 32, the voltage drop that occurs at the two ends thereof is 0.46V. Accordingly, emission of readout light L1 having improved light emission properties in the longitudinal direction thereof is enabled.

Figure 4:
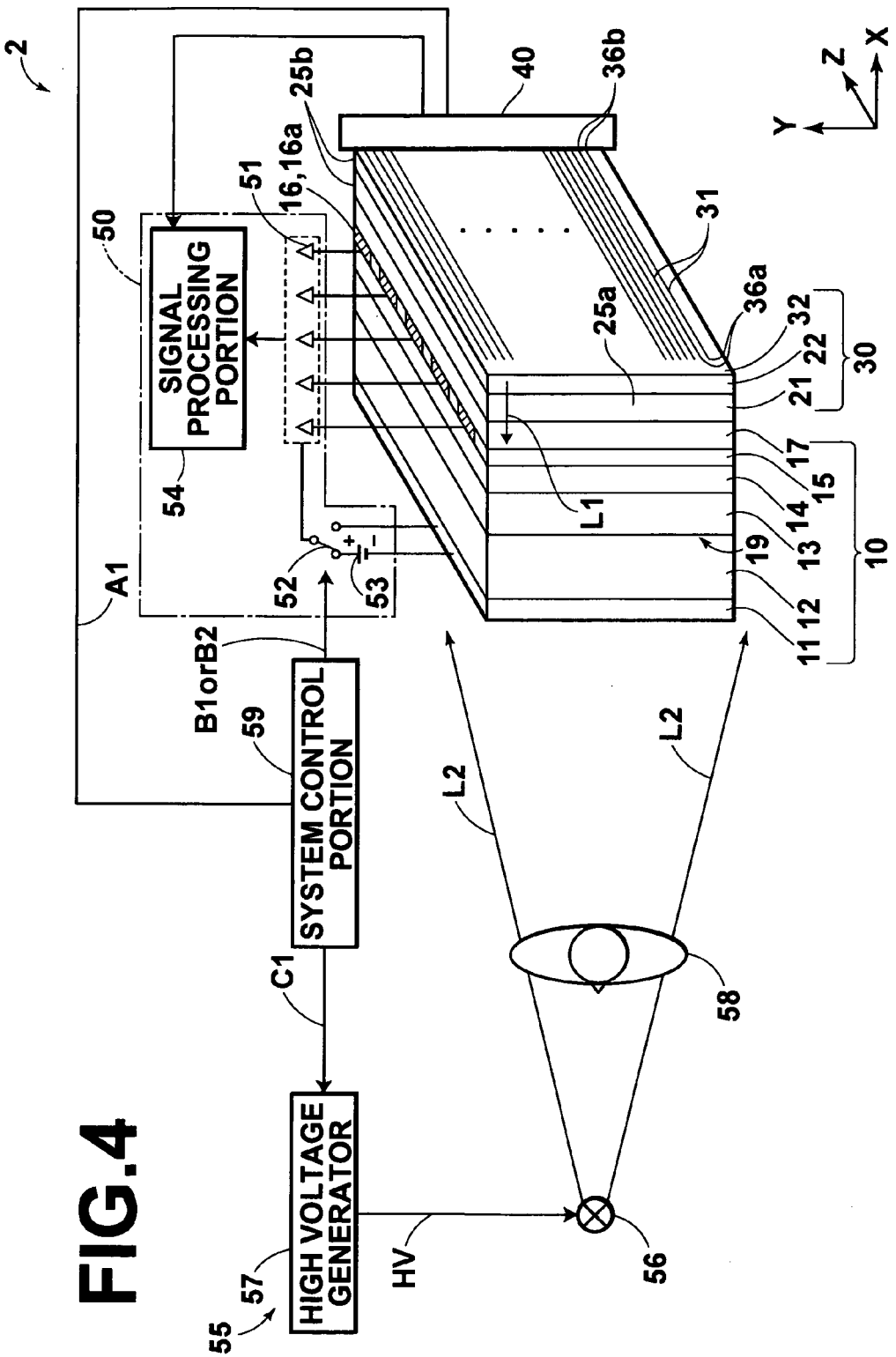
FIG. 4 is a schematic structural diagram that illustrates the image information recording/readout system according to a second embodiment of the present invention.

Next, an image information recording/readout system 2 according to a second embodiment of the present invention, in which a readout scanning exposure apparatus of the present invention is employed, will be described with reference to FIG. 4 and FIG. 5. FIG. 4 is a schematic structural diagram that illustrates the image information recording/readout system 2 according to the second embodiment of the present invention. Structural elements equivalent to those illustrated in FIG. 1 are denoted with the same reference numerals, and descriptions thereof will be omitted unless particularly necessary.

As illustrated in FIG. 4, the image information recording/readout system 2 comprises: an image recording medium 10, which is of a size 430 mm×430 mm; a panel light source 30, for scanning and exposing the image recording medium 10 with readout light L1; a scanning exposure control portion 40, for controlling the operation of the panel light source 30; a readout portion 50, for reading out the image information recorded on the image recording medium; a radiation emitting portion 55, for irradiating radiation L2, which is a recording light; and a system control portion 59, for controlling the scanning exposure control portion 40, the readout portion 50, and the radiation emitting portion 55.

Figure 5:
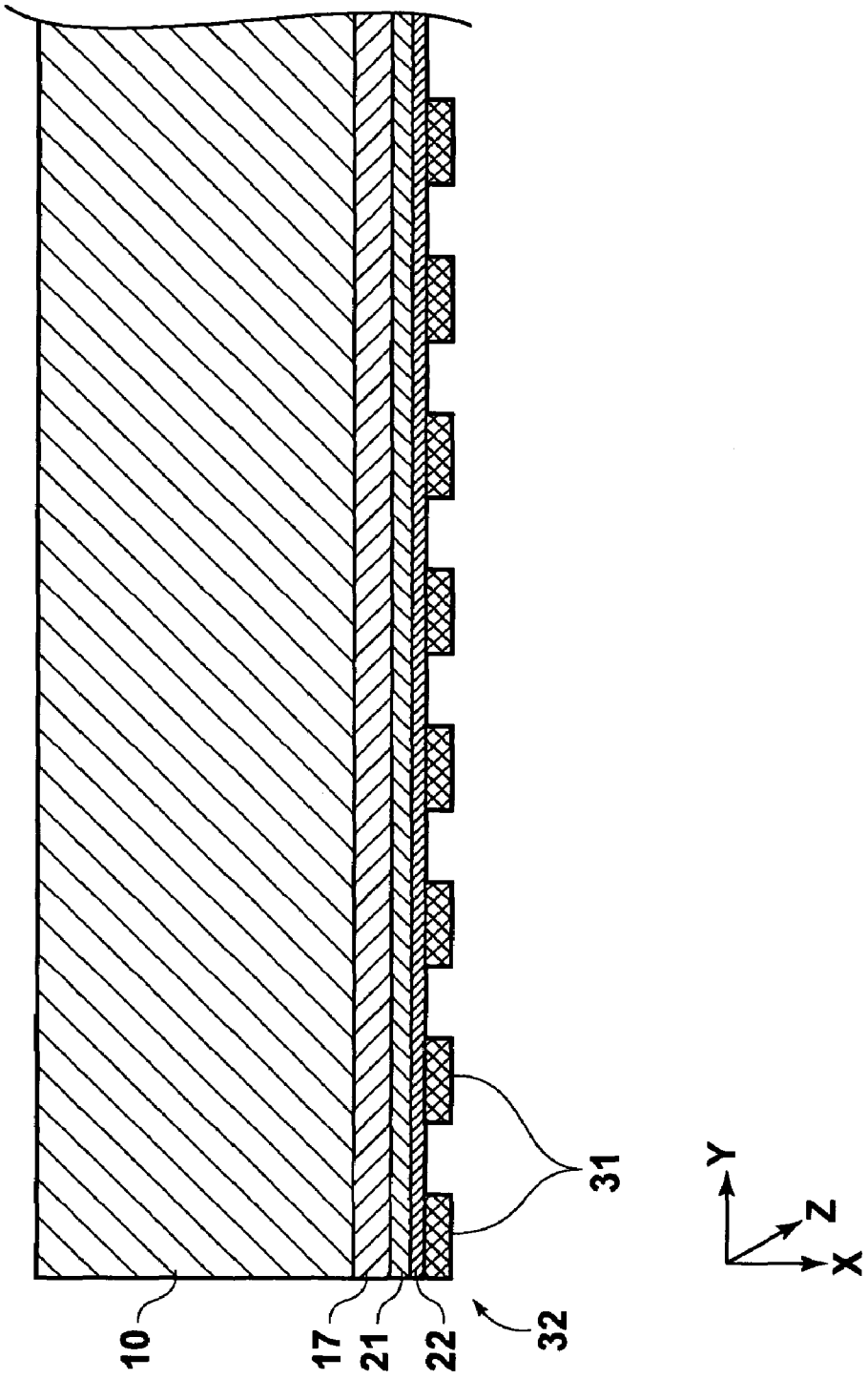
FIG. 5 is a partial sectional view of a panel light source.

FIG. 5 is a partial sectional view of the panel light source 30, taken along the XY plane. The panel light source 30 comprises: a planar light transmissive electrode 21 formed by an ITO film, having a thickness of 0.1 μm and a size of 430 mm (Z direction)×430 mm (Y direction); an EL layer 22, having a thickness of 0.1 μm and a size of 430 mm (Z direction)×430 mm (Y direction); and a linear electrode layer 32 formed by 4300 linear electrodes 31, which are arranged parallel with substantially equidistant gaps therebetween in the Z direction. Each linear electrode 31 is an aluminum electrode having a width of 50 μm, a length of 430 mm, and a thickness of 3 μm. As illustrated in FIG. 5, the planar light transmissive electrode 21 is provided in contact with the insulative layer 17, to correspond in position to the image recording medium 10. The light transmissive electrode 21, the EL layer 22, and the linear electrode layer 31 are stacked in this order in the X direction. The EL layer 22 is an organic EL layer. Alternatively, an inorganic EL layer may be employed. The light transmissive electrode 21 has ends 25a and 25b, in the Z direction. Of the ends 25a and 25b, a predetermined positive voltage is applied to the end 25a. Each of the linear electrodes 31 has ends 36a and 36b in the Z direction. Of the ends 36a and 36b, the ends 36b, which are at the opposite end of the linear electrodes 31 from the end 25a of the light transmissive electrode 21, are connected to the scanning exposure control portion 40. Note that the linear electrodes 31, the EL layer 22 and the light transmissive electrode 21 function as the line light source of the present invention.

The specific resistance of aluminum is $2.7 \times 10^{-6}$ Ω·cm. Because the linear electrodes 31 are 3 μm thick, the sheet resistance thereof is 0.009 Ω/sq. In addition, because the line width of the linear electrodes 31 is 50 μm and the length thereof is 430 mm, the resistance between the ends 36a and 36b is $$\frac{0.009 \cdot 430}{0.05} = 77.4 \ \Omega.$$

Meanwhile, the specific resistance of ITO is $4 \times 10^{-4}$ Ω·cm. Because the light transmissive electrode 21 is 0.1 μm thick, the sheet resistance thereof is 40 Ω/sq, and the resistance between the ends 24a and 25b of the light transmissive electrode 21 in the Z direction is 40 Ω.

The scanning exposure control portion 40 sequentially applies a predetermined DC voltage to the ends of each of the linear electrodes 31, when a control signal A1, commanding that readout scanning be performed, is input thereto. Thereby, the readout light L1 is sequentially emitted from the panel light source 30 at different timings.

The operation of the image information recording/readout system 2 is the same as that of the image information recording/readout system 1 illustrated in FIG. 1. Therefore, a detailed description thereof will be omitted.

As is clear from the above description, the present embodiment comprises the panel light source 30, which is constituted by: the ITO planar light transmissive electrode 21; the aluminum linear electrodes 31; and the EL layer 22, which is provided between the light transmissive electrode 21 and the linear electrodes 31. The resistance between the ends 25a and 25b of the light transmissive electride 21 is 40Ω, and the resistance between the ends 36a and 36b of the linear electrodes 31 is 77.4 Ω. For this reason, in the case that negative drive voltage is applied to the ends 36b of the linear electrodes 31, and positive voltage is applied to the end 25a of the light transmissive electrode 21 opposite therefrom, the ratio of the voltage drop that occurs between the two ends of the linear electrodes 31 in the longitudinal direction, with respect to the voltage drop that occurs between the portions of the light transmissive electrode 21 corresponding to the two ends of the linear electrodes 31 becomes approximately 0.5. Therefore, differences between the voltage drop that occurs in the linear electrodes 31 and the voltage drop that occurs in the light transmissive electrode are reduced. Accordingly, the potential differences between the light transmissive electrode 21 and the linear electrodes 31 are reduced at all positions along the longitudinal direction of the linear light beams. Thus, emission of readout light L1, which has little fluctuation in light emission in the longitudinal direction thereof, is enabled, even if driven with low voltage.

Figure 6:
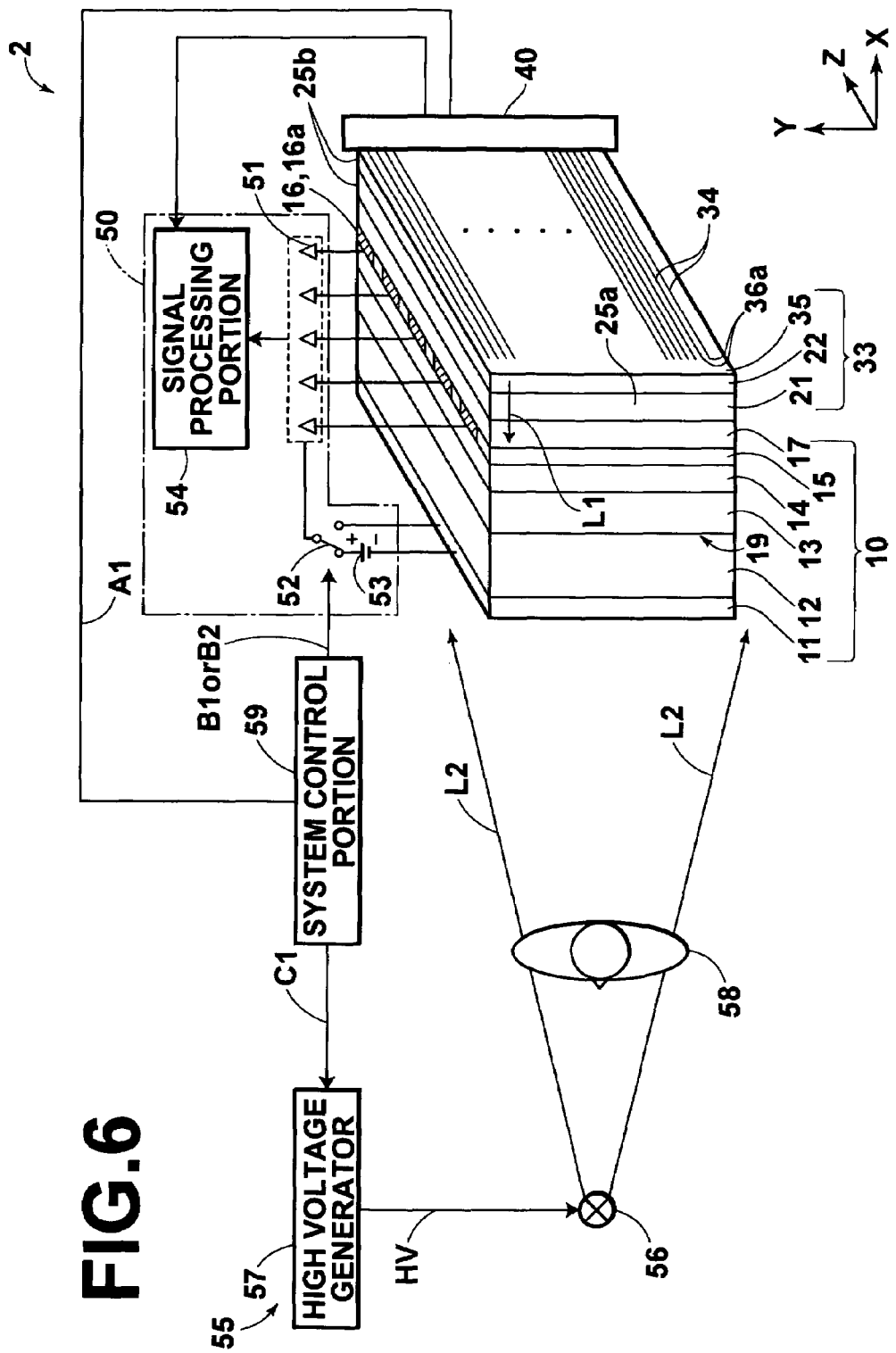
FIG. 6 illustrates a modification of the image information recording/readout system according to the second embodiment.

FIG. 6 illustrates a modification of the present embodiment. In this modification, a panel light source 33 is employed instead of the panel light source 30. The panel light source 33 comprises 4300 aluminum electrodes having a width of 50 μm and a thickness of 5.8 μm as linear electrodes 34. The linear electrodes 34 are arranged parallel to each other in the Z direction. The resistance between the two ends of the linear electrodes 34 in the Z direction becomes 40 Ω, which is equal to the resistance between the ends 25a and 25b of the light transmissive electrode 21. Because the resistance of the light transmissive electrode 21 and the resistance of the linear electrodes 34 are equal, a voltage drop that occurs in the linear electrodes 34 and a voltage drop that occurs in the light transmissive electrode are equal. Therefore, the potential differences between the light transmissive electrode 21 and the linear electrodes 34 are substantially equal at all positions along the longitudinal direction of the linear light beams. Thus, emission of readout light L1, which has substantially no fluctuations in light emission in the longitudinal direction thereof, is enabled, even if driven with low voltage.

Figure 7:
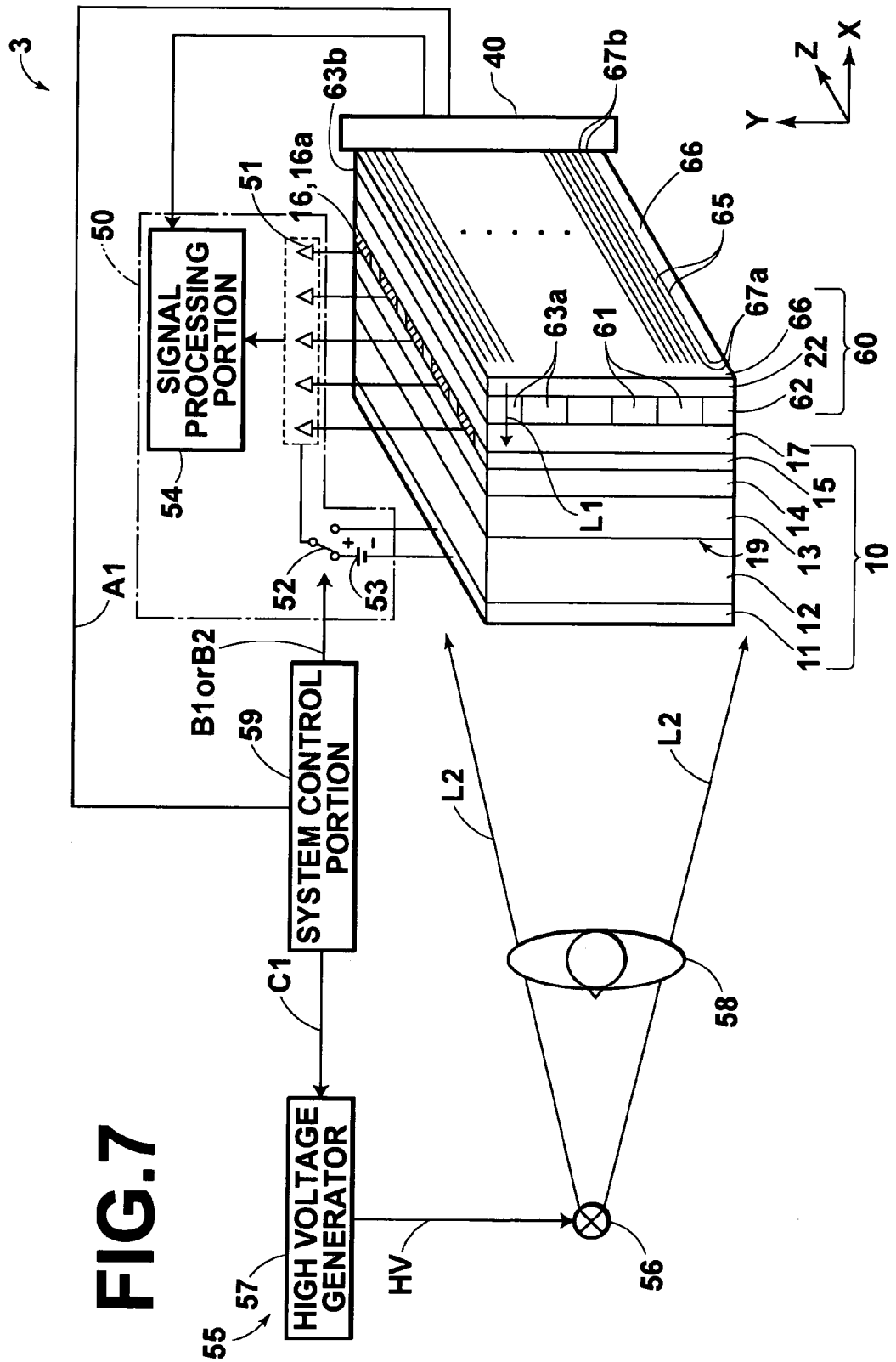
FIG. 7 is a schematic structural diagram that illustrates the image information recording/readout system according to a third embodiment of the present invention.

Next, an image information recording/readout system 3 according to a third embodiment of the present invention, in which a readout scanning exposure apparatus of the present invention is employed, will be described with reference to FIG. 7, FIG. 8 and FIG. 9. FIG. 7 is a schematic structural diagram that illustrates the image information recording/readout system 3 according to the third embodiment of the present invention. Structural elements equivalent to those illustrated in FIG. 1 are denoted with the same reference numerals, and descriptions thereof will be omitted unless particularly necessary.

As illustrated in FIG. 7, the image information recording/readout system 2 comprises: an image recording medium 10, which is of a size 430 mm (Z direction)×430 mm (Y direction); a panel light source 60, for scanning and exposing the image recording medium 10 with readout light L1; a scanning exposure control portion 40, for controlling the operation of the panel light source 60; a readout portion 50, for reading out the image information recorded on the image recording medium; a radiation emitting portion 55, for irradiating radiation L2, which is a recording light; and a system control portion 59, for controlling the scanning exposure control portion 40, the readout portion 50, and the radiation emitting portion 55.

Figure 8:
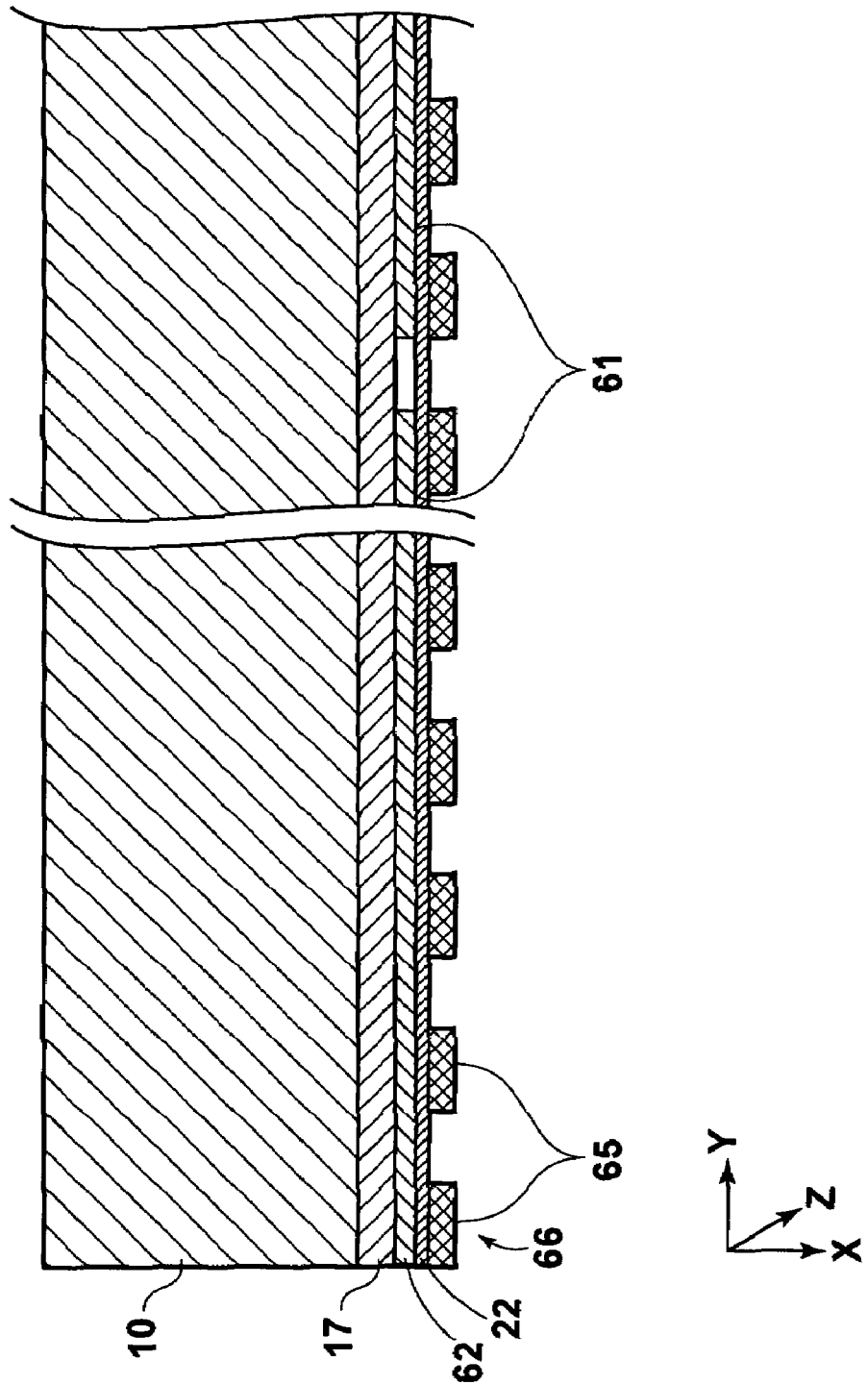
FIG. 8 is a partial sectional view of a panel light source.

FIG. 8 is a partial sectional view of the panel light source 60, taken along the XY plane. The panel light source 60 comprises: a light transmissive electrode layer 62, constituted by 227 planar light transmissive electrodes 61 formed by ITO film, each having a thickness of 0.4 μm and a size of 430 mm (Z direction)×1.85 mm (Y direction), arranged in the Y direction at 1.9 mm intervals; an EL layer 22, having a thickness of 0.1 μm and a size of 430 mm (Z direction)×430 mm (Y direction); and a linear electrode layer 66 formed by 4300 linear electrodes 65, which are arranged parallel with substantially equidistant gaps therebetween in the Z direction. Each linear electrode 65 is an aluminum electrode having a width of 50 μm, a length of 430 mm, and a thickness of 0.1 μm. FIG. 9 is a model diagram that illustrates the relationship between the light transmissive electrodes 61 and the linear electrodes 65, viewed from the X direction. As illustrated in FIG. 9, 18 linear electrodes 65 correspond to a single light transmissive electrode 61.

As illustrated in FIG. 8, each of the planar light transmissive electrodes 61 is provided in contact with the insulative layer 17, to correspond in position to the image recording medium 10. The light transmissive electrode layer 62, the EL layer 22, and the linear electrode layer 66 are stacked in this order in the X direction. Each of the light transmissive electrodes 61 have ends 63a and 63b, in the Z direction. Of the ends 63a and 63b, the end 63a is grounded. Each of the linear electrodes 65 has ends 67a and 67b in the Z direction. Of the ends 67a and 67b, the ends 67b, which are at the opposite end of the linear electrodes 65 from the end 63a of the light transmissive electrode 61, are connected to the scanning exposure control portion 40.

Note that the specific resistance of aluminum is 2.7×10$^{-6}$ Ω·cm, and the resistance between the end 67a and the end 67b of each of the linear electrodes 65 is 2.3 KΩ. For this reason, in the case that a 2 mA current flows through the linear electrode 65, the voltage drop between the end 67a and the end 67b is 4.6V.

Meanwhile, the specific resistance of ITO is 4×10$^{-4}$ Ω/cm, and the resistance between the ends 63a and 63b of the light transmissive electrodes 61 in the Z direction is 2.3 KΩ. For this reason, in the case that a 2 mA current flows through the light transmissive electrode 61, the voltage drop between the end 63a and the end 63b is also 4.6V. Each of the light transmissive electrodes 61 is grounded at the end 67a, which is at the end opposite from the drive side of the linear electrodes 65. Therefore, the voltage drops cancel each other out, and the potential differences between the light transmissive electrodes 61 and the linear electrodes 65 are substantially equal at all positions along the longitudinal direction of the linear electrodes 65. Thus, emission of readout light L1, which has further reduced fluctuations in light emission in the longitudinal direction thereof, is enabled.

FIG. 10 is a graph that illustrates the relationship between the distance from an end (hereinafter, referred to as "power supply end") of a linear electrode 65, to which a 65V voltage is applied, and a voltage, which is applied to the EL layer 22. In the present embodiment, a blue light emitting layer formed by spiro-NPB, spiro-DPVBI, and Cs doped BCP is employed as the EL layer 22. Resistance Rd(V) of the EL layer 22 per unit length can be expressed by the following equation. Note that Rd(V) is dependent on voltage V, and transforms in a nonlinear manner.

$$Rd(V) = \frac{V}{0.6481 \cdot 10^{-6} \cdot e^{0.3451 \cdot V(x)^{\frac{3}{7}}}}$$

In addition, if the resistance of the linear electrodes 65 per unit length is designated as Ra, the resistance of the light transmissive electrodes 61 per unit length is designated as Rc, the distance from the power supply end is designated as x, and the voltage applied to the EL layer at a position at distance x is designated as V(x), the following differential equation is satisfied.

$$V''(x) - (Ra - Rc) \cdot \frac{1}{\frac{4}{1 \cdot 0.05} \cdot \frac{V(x)}{0.6481 \cdot 10^{-6} \cdot e^{0.3451 \cdot V(x)^{\frac{3}{7}}}}} \cdot V(x) = 0$$

A graph such as that illustrated in FIG. 10 can be obtained by solving the above differential equation, employing the prefixed function of Mathcad.

Figure 11:
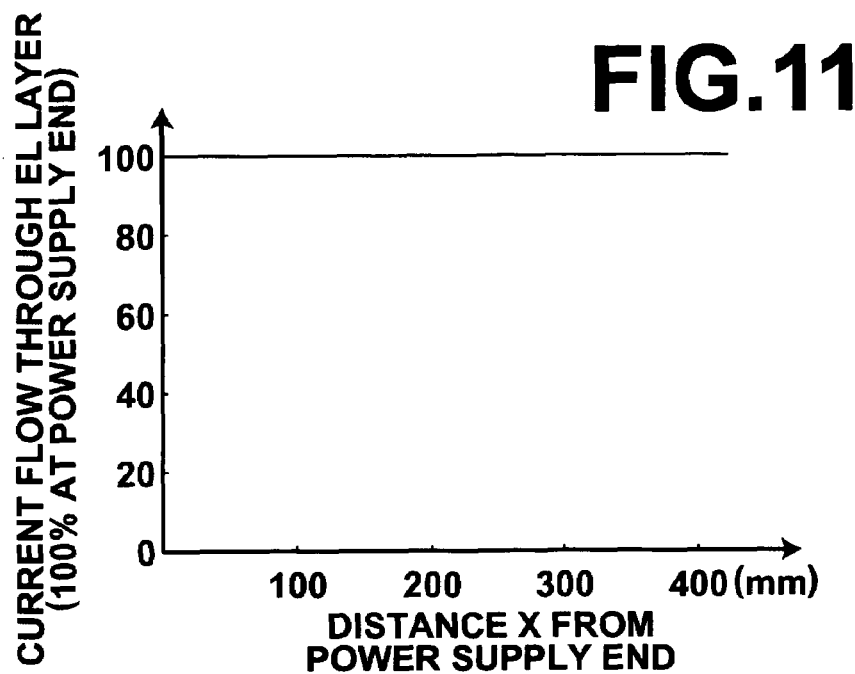
FIG. 11 is a graph that illustrates the relationship between the distance from the power supply end and electric current that flows through the EL layer.

As can be understood from the graph of FIG. 10, the voltage hardly drops across the entire length of the electrodes. FIG. 11 is a graph that illustrates the relationship between the distance x from the power supply end and the electric current D(x) that flows through the EL layer. It can be understood from the graph of FIG. 11 that a substantially uniform amount of electric current flows through the EL layer across the entire length of the electrodes. Therefore, light emission from the EL layer is also substantially uniform.

A method for deriving the width wc of the light transmissive electrodes 61 will be described. A case is assumed wherein: the linear electrodes 65 are aluminum electrodes having a width (wa) of 50 μm and a thickness of 0.1 μm and which are arranged at intervals of 100 μm (pitch P=0.1 mm); and the light transmisive electrodes 61 are formed by ITO film having a thickness of 0.4 μm. In this case, the sheet resistance ra of the linear electrodes 65 is 0.27 Ω/sq, and the sheet resistance rc of the light transmissive electrodes 61 is 10 Ω/sq.

Further, the theoretically ideal line width wc of the light transmissive electrode is:

$$wc = \frac{rc \cdot wa}{ra}.$$

However, it is desirable that the width wc of the light transmissive electrodes 61 be set such that gaps are not formed at positions corresponding to opposing linear electrodes 65. In the case that a gap between the light transmissive electrodes 61 opposes a linear electrode 65, it becomes difficult to accurately read out image information from that linear electrode 65. The width of the light transmissive electrodes 61 is set in the following manner, to avoid such trouble. A method for calculating the width wc in the case that gaps having a gap width of 50 μm, for example, are necessary between the light transmissive electrodes 61 will be described. First, the maximum integer n that satisfies the equation $$n < \frac{wa \cdot rc}{ra \cdot P} = \frac{10 \cdot 0.05}{0.27 \cdot 1}$$

is derived. In the present embodiment, n=18. If the width wc satisfies the equation wc≧n·P−wi=18·0.1−0.05=1.75 mm, voltage drops within the light transmissive electrodes 61 can be suppressed. Accordingly, emission of linear light beams having improved light emission properties in the longitudinal direction is enabled.

Further, if the width wc satisfies the equation 1.75 mm≦wc<(n+1)·P+wa=(18+1)·0.1+0.05=1.95, voltage drops within the linear electrodes 65 and voltage drops within the light transmissive electrodes 61 partially cancel each other out. Accordingly, emission of linear light beams, having reduced fluctuations in light emission, is enabled.

Still further, an even more appropriate line width wc can be determined on a case by case basis, as follows.

Assuming that $$\frac{rc \cdot wa}{ra} = A:$$

In the case that $$A < n \cdot P + \frac{wa - wi}{2},$$

wc′=n·P−wi.

In the case that $$n \cdot P + \frac{wa - wi}{2} \leq A < n \cdot P + wa,$$

wc′=n·P+wa.

In the case that n·P+wa≦A<(n+1)·P−wi, $$wc' = A = \frac{rc \cdot wa}{ra}.$$

In the case that $$(n+1) \cdot P - wi \leq A < (n+1) \cdot P + \frac{wa - wi}{2},$$

wc′=(n+1)·P−wi.

In the case that $$A \geq (n+1) \cdot P + \frac{wa - wi}{2},$$

wc′=(n+1)·P+wa.

In the present embodiment, because gaps having a width of 50 µm are necessary between the light transmissive electrodes 61, (n+1)·P−wi=1.85;

A=1.852; and $$(n+1) \cdot P + \frac{wa - wi}{2} = 1.9.$$

Therefore, the width wc′=A=1.852.

Positive voltage is applied to the ends 63a of the light transmissive electrodes 61, which are at the end opposite from the drive side of the linear electrodes 65. Therefore, the voltage drops cancel each other out, and the potential differences between the light transmissive electrodes 61 and the linear electrodes 65 are substantially equal at all positions along the longitudinal direction of the linear electrodes 65. Thus, emission of readout light L1, which has little fluctuation in light emission in the longitudinal direction thereof, is enabled.

The resistances of the linear electrodes 65 and the light transmissive electrodes 61 can be coordinated simply by forming the light transmissive electrode 61 in a divided manner. In addition, the thickness of the linear electrodes 65 can be made as little as 0.1 µm. Therefore, the total thickness of the light transmissive electrodes 61, the EL layer 22 and the linear electrodes 65 combined is approximately 1 µm. Accordingly, an extremely thin panel light source 60 can be realized.

Note that the operation of the image information recording/readout system 3 is the same as that of the image information recording/readout system 1 illustrated in FIG. 1. Therefore, a detailed description thereof will be omitted.

Figure 12:
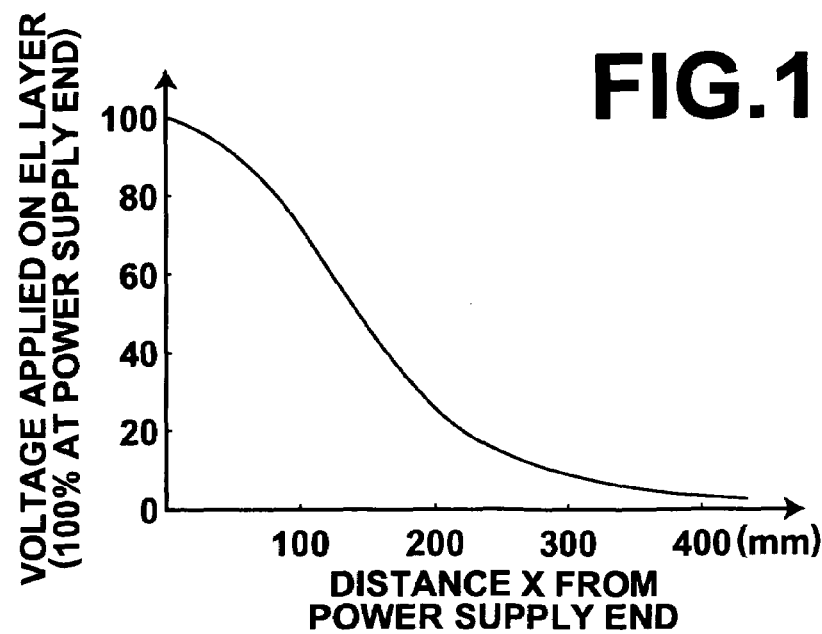
FIG. 12 is a graph that illustrates the relationship between the distance from a power supply end of a linear electrode and a voltage, which is applied to an EL layer.

Consider a first modification to the present embodiment, in which the width wc is 0.95 mm. In this case, the resistance of the light transmissive electrodes 61 will be twice the resistance of the linear electrodes 65. FIG. 12 is a graph that illustrates the relationship between the distance x from the power supply end and the electric current D(x) that flows through the EL layer. It can be seen from the graph of FIG. 12 that the EL layer emits light across the entire length of the electrodes. However, because light emission is reduced at the end opposite from the power supply end, it is preferable that data of FIG. 12 is employed to correct signal values of the read out image signals.

Figure 13:
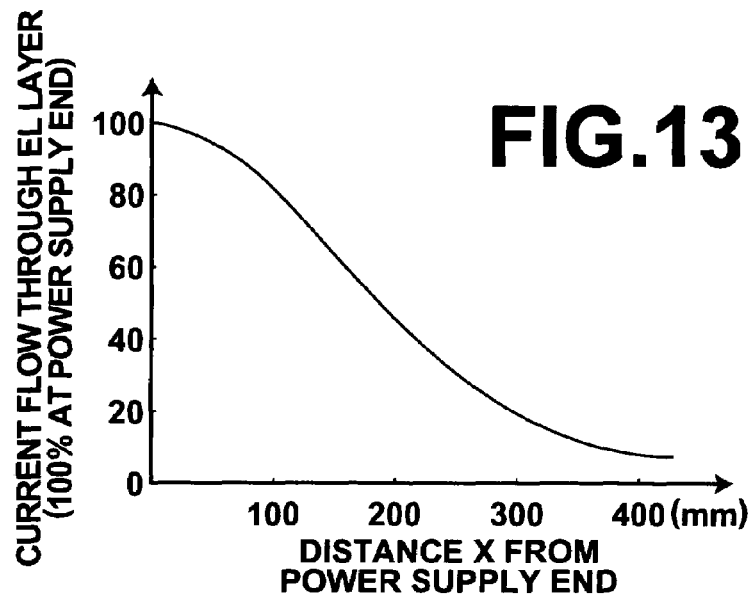
FIG. 13 is a graph that illustrates the relationship between the distance from the power supply end and electric current that flows through the EL layer.

Now, consider a second modification to the present embodiment, in which the width wc is 3.65 mm. In this case, the resistance of the light tranmissive electrodes 61 will be half the resistance of the linear electrodes 65. FIG. 13 is a graph that illustrates the relationship between the distance x from the power supply end and the electric current D(x) that flows through the EL layer. It can be seen from the graph of FIG. 13 that the EL layer emits light across the entire length of the electrodes. However, because light emission is reduced at the end opposite from the power supply end, it is preferable that data of FIG. 13 is employed to correct signal values of the read out image signals.

As evidenced by the first and second modifications above, by setting the ratio of the resistance of the linear electrodes with respect to the resistance of the light transmissive electrodes to be 0.5 or greater and 2 or less, voltage drops that occur in the linear electrodes and voltage drops that occur in the light transmissive electrodes partially cancel each other out. Accordingly, potential differences between the light transmissive electrodes and the linear electrodes are reduced at all positions along the longitudinal direction of the linear light beams. Thus, a line light source capable of emitting linear light beams, which have little fluctuation in light emission in the longitudinal direction thereof, even if driven with low voltage, is realized. Note that in the case that the length of the line light source is short, emission of linear light beams, having little fluctuation in the longitudinal direction thereof, is enabled as well.

Figure 14:
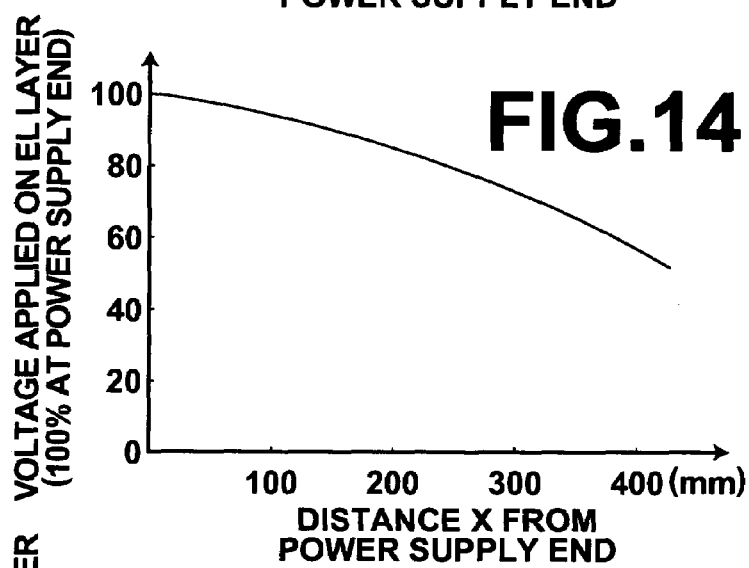
FIG. 14 is a graph that illustrates the relationship between the distance from the power supply end and electric current that flows through the EL layer.

Consider a third modification to the present embodiment, in which the width wc is 1.69 mm. In this case, the resistance of the light transmissive electrodes 61 will be 1.1 times the resistance of the linear electrodes 65. FIG. 14 is a graph that illustrates the relationship between the distance x from the power supply end and the electric current D(x) that flows through the EL layer. It can be seen from the graph of FIG. 14 that the EL layer emits light across the entire length of the electrodes, and that approximately half the amount of light emitted at the power supply end is emitted at the end opposite thereto. It is preferable that data of FIG. 14 is employed to correct signal values of the read out image signals. Because approximately half the amount of light emitted at the power supply end is emitted at the end opposite thereto, correction processes are facilitated.

Figure 15:
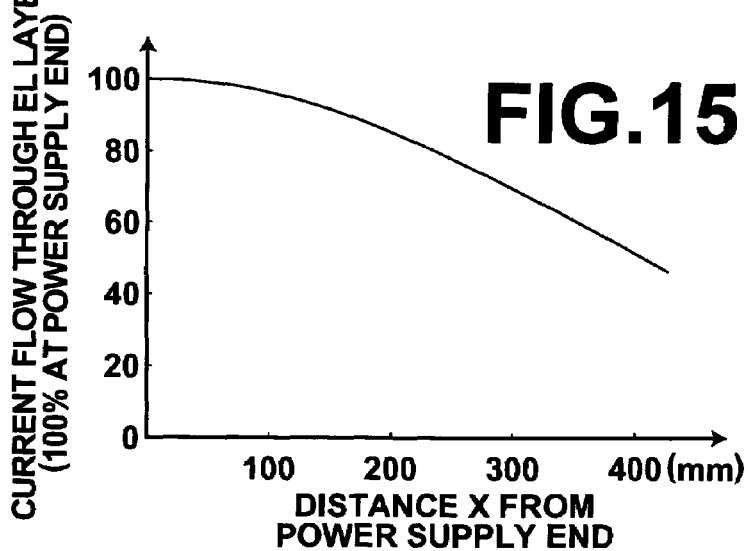
FIG. 15 is a graph that illustrates the relationship between the distance from the power supply end and electric current that flows through the EL layer.

Now, consider a fourth modification to the present embodiment, in which the width wc is 2.05 mm. In this case, the resistance of the light tranmissive electrodes 61 will be 0.9 times the resistance of the linear electrodes 65. FIG. 15 is a graph that illustrates the relationship between the distance x from the power supply end and the electric current D(x) that flows through the EL layer. It can be seen from the graph of FIG. 15 that the EL layer emits light across the entire length of the electrodes, and that approximately half the amount of light emitted at the power supply end is emitted at the end opposite thereto. It is preferable that data of FIG. 15 is employed to correct signal values of the read out image signals. Because approximately half the amount of light emitted at the power supply end is emitted at the end opposite thereto, correction processes are facilitated.

As evidenced by the third and fourth modifications above, by setting the ratio of the resistance of the linear electrodes with respect to the resistance of the light transmissive electrodes to be 0.9 or greater and 1.1 or less, differences in voltage drops that occur in the linear electrodes and voltage drops that occur in the light transmissive electrodes are reduced. Accordingly, potential differences between the light transmissive electrodes and the linear electrodes are reduced at all positions along the longitudinal direction of the linear light beams. Thus, a line light source capable of emitting linear light beams, which have little fluctuation in light emission in the longitudinal direction thereof, even if driven with low voltage, is realized. Note that in the case that the length of the line light source is short, emission of linear light beams, having little fluctuation in the longitudinal direction thereof, is enabled as well.

Figure 16:
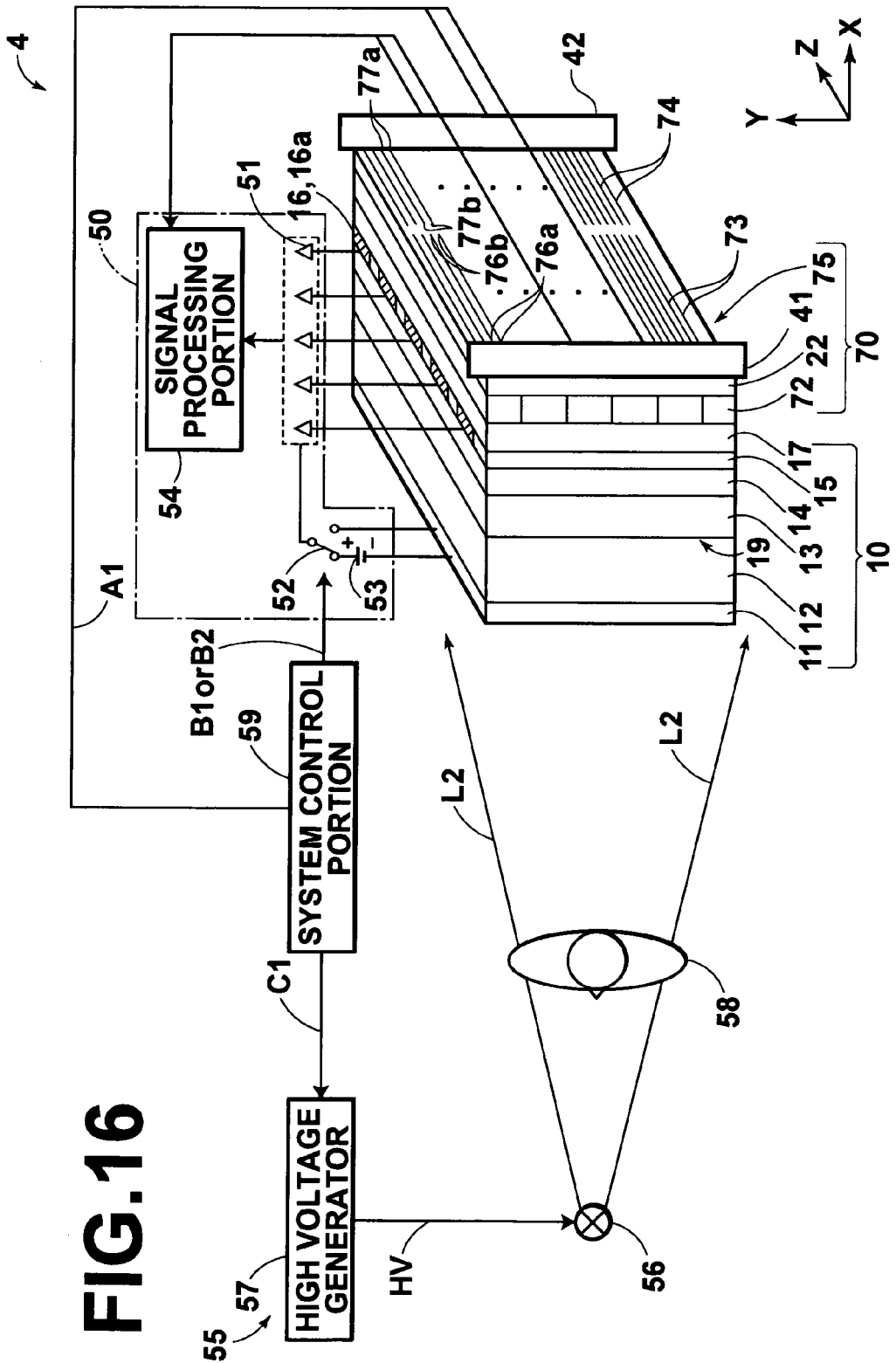
FIG. 16 is a schematic structural diagram that illustrates an image information recording/readout system according to a fourth embodiment of the present invention.
Figure 17:
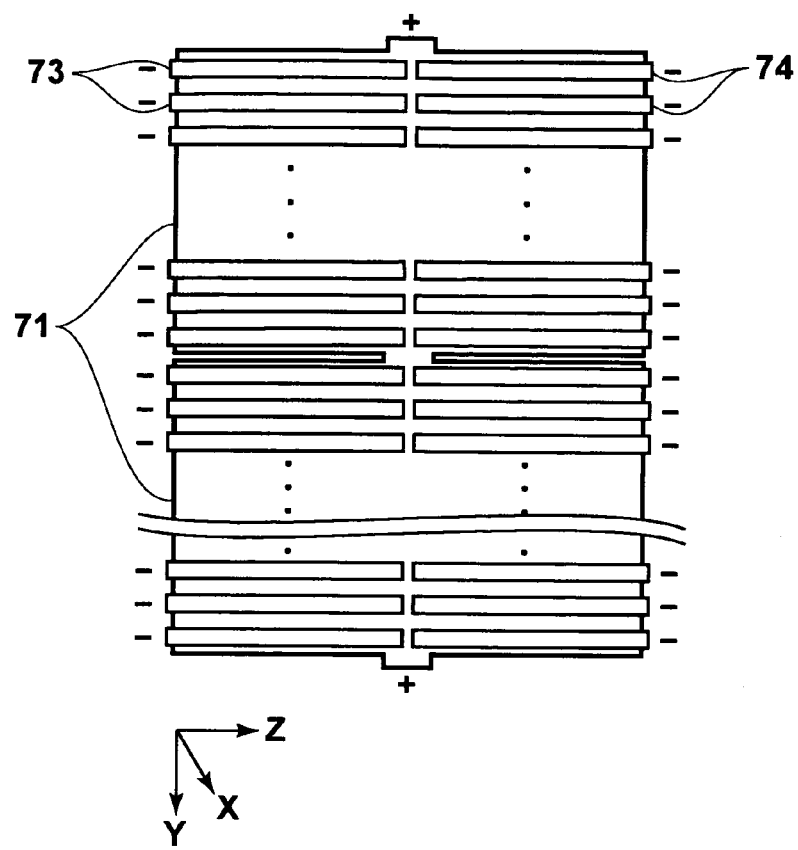
FIG. 17 is a model diagram that illustrates the relationship between light transmissive electrodes and linear electrodes.

An image information recording/readout system 4 according to a fourth embodiment of the present invention will be described with reference to FIG. 16 and FIG. 17. FIG. 16 is a schematic structural diagram that illustrates the construction of the image information recording/readout system 4. Structural elements equivalent to those illustrated in FIG. 1 are denoted with the same reference numerals, and descriptions thereof will be omitted unless particularly necessary.

As illustrated in FIG. 16, the image information recording/readout system 2 comprises: an image recording medium 10; a panel light source 70, for scanning and exposing the image recording medium 10 with readout light L1; scanning exposure control portions 41 and 42, for controlling the operation of the panel light source 70; a readout portion 50, for reading out the image information recorded on the image recording medium; a radiation emitting portion 55, for irradiating radiation L2, which is a recording light; and a system control portion 59, connected to the scanning exposure control portions 41 and 42, the readout portion 50, and the radiation emitting portion 55.

The panel light source 70 comprises: a light transmissive electrode layer 72, constituted by 60 planar light transmissive electrodes 71 formed by ITO film, each having a thickness of 0.1 μm and a size of 430 mm (Z direction)×7.35 mm (Y direction), arranged in the Y direction at 7.4 mm intervals; an EL layer 22; and a linear electrode layer 75, formed by 4300 linear electrodes 74, which are 2190 mm long and arranged parallel with substantially equidistant gaps therebetween in the Z direction and 4300 linear electrodes 73, which are 2190 mm long and arranged parallel with substantially equidistant gaps therebetween in the Z direction. Each of the linear electrodes 73 and 74 is an aluminum electrode having a width of 50 μm and a thickness of 0.1 μm. The linear electrodes 73 and 74 are arranged at 100 μm intervals. The linear electrodes 73 have ends 76a and 76b in the Z direction. Of the ends 76a and 76b, the ends 76a, which are provided toward the exterior, are connected to the scanning exposure control portion 41. The linear electrodes 74 have ends 77a and 77b in the Z direction. Of the ends 77a and 77b, the ends 77am which are provided toward the exterior, are connected to the scanning exposure control portion 42. FIG. 17 is a model diagram that illustrates the relationship between the light transmissive electrodes 71 and the linear electrodes 73 and 74, viewed from the X direction. As illustrated in FIG. 17, adjacent light transmissive electrodes 71 are connected to each other at their central portions in the Z direction. The same predetermined positive voltage is applied to the exterior central portions of the light transmissive electrodes 71, which are provided at the two ends in the Y direction. In addition, 74 linear electrodes 73 and 74 linear electrodes 74 correspond to a single light transmissive electrode 71.

The scanning exposure control portion 41 sequentially applies a predetermined DC voltage to the ends 76a of each of the linear electrodes 73, when a control signal A1, commanding that readout scanning be performed, is input thereto from the system control portion 59. Thereby, readout light L1 is sequentially emitted from the panel light source 70 at different timings.

The scanning exposure control portion 42 sequentially applies a predetermined DC voltage to the ends 77a of each of the linear electrodes 74, when a control signal A1, commanding that readout scanning be performed, is input thereto from the system control portion 59. Thereby, the readout light L1 is sequentially emitted from the panel light source 70 at different timings. Drive voltages maybe applied to the linear electrodes 73 and the linear electrodes 74 at different timings, or simultaneously. In the case that the drive voltages are applied simultaneously, the linear electrodes 73 and the linear electrodes 74 may be connected to each other.

Note that the resistance between the ends of the linear electrodes 73 and the linear electrodes 74 are both 1.2 KΩ. The resistance between portions of the light transmissive electrodes 71 that correspond to the ends of the linear electrodes 73 and 74 is also 1.2 KΩ. In addition, predetermined positive voltages are applied to the central portions of the light transmissive electrodes 71 at a portion thereof which is opposite from the drive side of the linear electrodes 73 and 74. Therefore, voltage drops that occur in the linear electrodes 73 or 74 and voltage drops that occur in the light transmissive electrodes 71 cancel each other out. Thereby, potential differences between the light transmissive electrodes 71 and the linear electrodes 73 or 74 become substantially equal at all positions along the longitudinal direction thereof. Accordingly, emission of readout light L1, which has little fluctuation in light emission in the longitudinal direction thereof, is enabled.

Note that the operation of the image information recording/readout system 4 is the same as that of the image information recording/readout system 1 illustrated in FIG. 1, except for the manner in which the readout light L1 is emitted. Therefore, a detailed description thereof will be omitted.

In addition, in the embodiments described above, the photoconductive layers record image signals by exhibiting conductivity when irradiated with the recording radiation L2. However, the photoconductive layers of the present invention are not necessarily limited to those of this type. The photoconductive layers may be of the type that exhibit conductivity when irradiated with light, which is generated due to excitation by the recording radiation L2. In this case, a so called wavelength converting layer, such as an X-ray scintillator that converts the wavelength of recording radiation to light of a difference wavelength, such as blue light, is stacked on the surface of the first electrode layer. Cesium iodide (CsI), for example, may be employed as the wavelength converting layer. In addition, the first electrode layer and the first electrode layer and the first insulative layer are those which are transmissive with respect to light, which is generated at the wavelength converting layer due to excitation by the recording radiation.

Figure 18:
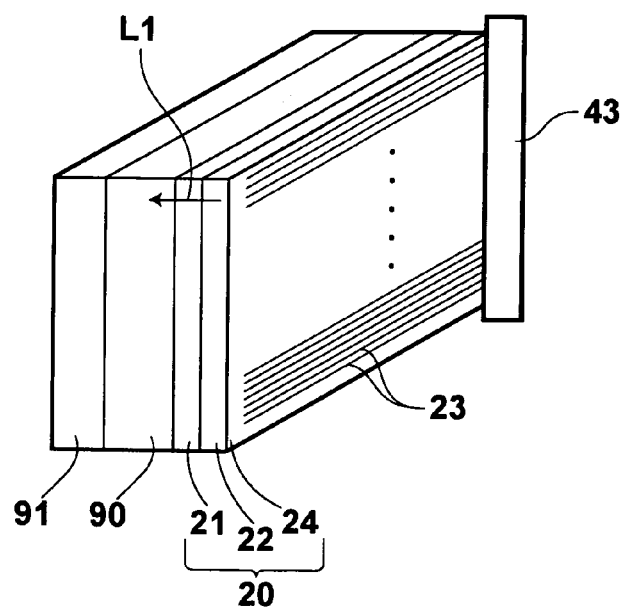
FIG. 18 is a schematic perspective view of a panel light source and a stimulable phosphor recording sheet, which are employed in an image information recording/readout system according to the fifth embodiment.

Next, a fifth embodiment, to which the scanning exposure apparatus of the present invention is applied, will be described with reference to FIG. 18. FIG. 18 is a schematic perspective view of a panel light source 20 and a stimulable phosphor recording sheet 90, which are employed in the image information recording/readout system 5 according to the fifth embodiment.

The image information recording/readout system 5 comprises: the stimulable phosphor sheet 90, on which radiation image information has been recorded; the panel light source 20, for scanning and exposing the stimulable phosphor sheet 90 with readout light L1; a scanning exposure control portion 43; a photodetector 91, for detecting stimulated phosphorescence M, which is emitted by the stimulable phosphor sheet 90 when irradiated with readout light L1; and a signal processing portion (not shown), to which the photodetector 91 is connected. Note that the photodetector 91 is provided on the side of the stimulable phosphor sheet 90 opposite from the panel light source 20. The photodetector 91 comprises a great number of photoelectric conversion elements. Each of the photoelectric conversion elements detects the stimulated phosphorescence M emitted from positions (pixels) of the stimulable phosphor sheet 90 corresponding thereto. Specific examples of the photoelectric conversion elements are: amorphous silicon sensors, CCD sensors, MOS sensors, and the like. The photodetector 90 may be configured as a two dimensional sensor as illustrated in FIG. 18, or may be configured as a one dimensional sensor, which is moved in synchrony with the scanning readout light L1.

Next, the operation of the image information recording/readout system 5 will be described. Readout light L1, emitted from the panel light source 20 in the form of linear light beams, scan and expose the stimulable phosphor sheet 90 by control of the scanning exposure control portion 43. Stimulated phosphorescence M is emitted from the portions of the stimulable phosphor sheet 90, which are irradiated with the readout light L1, corresponding to radiation image information recorded thereat. A portion of the stimulated phosphorescence M enters the photodetector 91. The stimulated phosphorescence M that enters the photodetector 91 are amplified and photoelectrically converted by each photoelectric conversion element, and output to the signal processing portion as image signals of pixels, to which the photoelectric conversion elements correspond.

Note that the EL layer 22 of the panel light source is that which outputs light at a wavelength appropriate for causing stimulated phosphorescence to be emitted from the stimulable phosphor sheet 90. The same advantageous effects as those of the first embodiment may be obtained by the present embodiment. Note also that any of the panel light sources 27, 30, 33, 60, and 70 may be employed in lieu of the panel light source 20.

Figure 19:
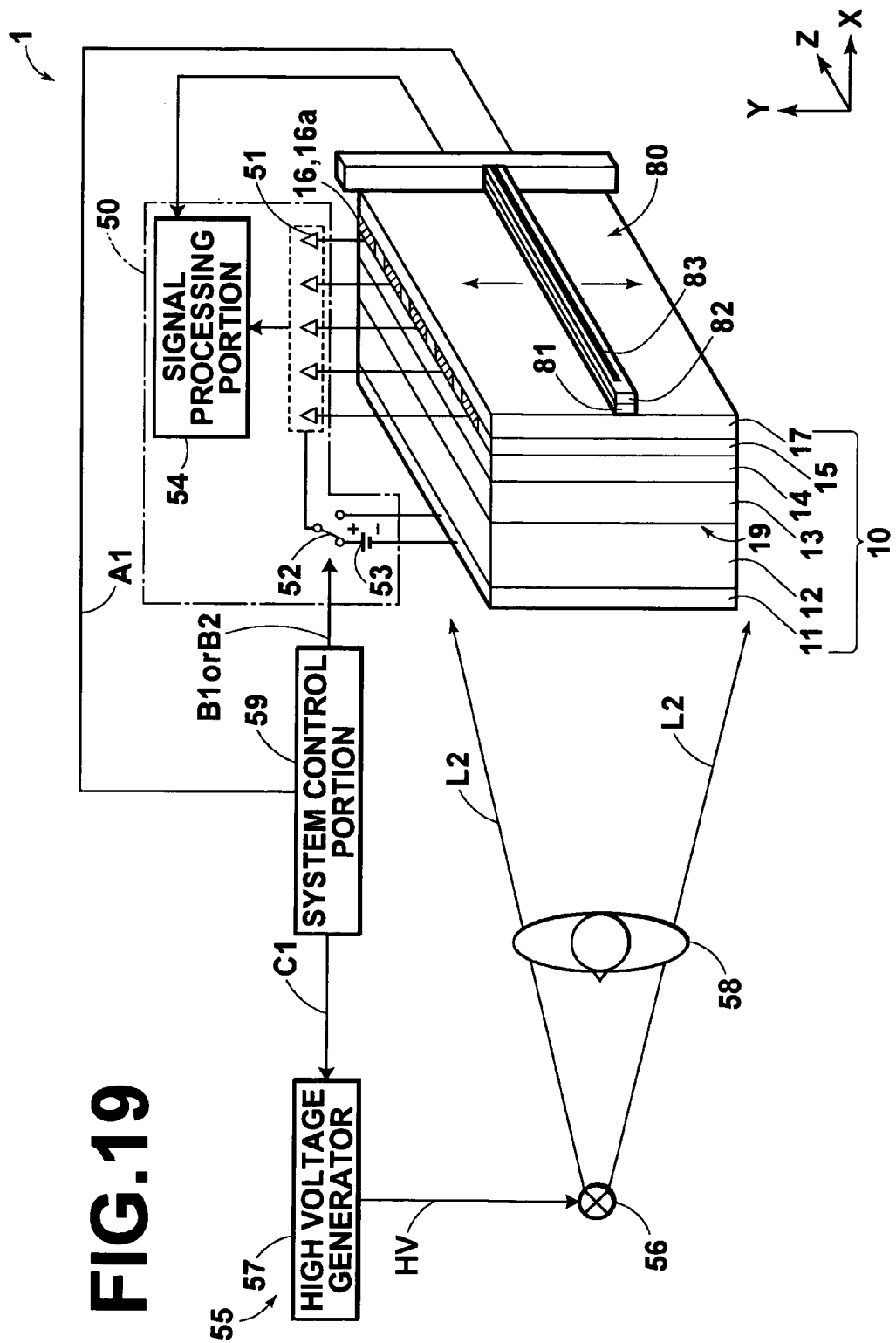
FIG. 19 is a schematic structural diagram that illustrates a modification of the image information recording/readout systems of the present invention.

Note that the embodiments above employ panel light sources having great numbers of line light sources provided therein. However, the present invention is not limited to this configuration, and may employ a light source that scans a single line light source mechanically. For example, as illustrated in FIG. 19, a line light source 80 comprising: an EL layer 82 having a thickness of 0.1 μm, a length of 430 mm (Z direction), and a width of 7.35 mm (Y direction); and a linear electrode 83 formed by an aluminum electrode having a thickness of 0.1 μm, a length of 430 mm (Z direction), and a width of 7.35 mm (Y direction) may be employed. The image recording medium 10 may be scanned and exposed with readout light L1 by mechanically scanning the line light source 80 in the Y direction, with a mechanical scanning means (not shown).

What is claimed is:

1. A scanning exposure apparatus, comprising:
a panel light source for sequentially emitting linear light beams; and
an exposure control means for controlling the emission of light by the panel light source, wherein:
the panel light source comprises:
at least one planar light transmissive electrode;
a plurality of linear electrodes, which are arranged in a first direction; and
an EL layer, provided between the light transmissive electrode and the linear electrodes;
the exposure control means causes electric current to flow through the linear electrodes in a sequential manner, thereby causing electric current to flow in the EL layer provided between the light transmissive planar electrode and the linear electrodes, to cause sequential emission of the linear light beams; and
scanning exposure is performed in the first direction, which is perpendicular to the longitudinal direction of the linear light beams, wherein
the linear electrodes are formed by thin films having a sheet resistance ra, widths wa, and which are arranged at a pitch P;
the at least one light transmissive electrode is formed by a plurality of rectangular thin films having a sheet resistance rc, which are arranged in the first direction at substantially equidistant gaps having a width wi; and
the width wc of the light transmissive electrode satisfies the equation:
wc≧n·P−wi, wherein n is the maximum integer that satisfies the equation:

$$n < \frac{wa \cdot rc}{ra \cdot P}.$$

2. A scanning exposure apparatus as defined in claim 1, wherein:
the resistance of the light transmissive electrode and the resistance of the linear electrodes are substantially equal.

3. A scanning exposure apparatus as defined in claim 1, wherein:
the width wc satisfies the equation:
$$wc \leq (n+1) \cdot P + wa.$$

4. An image information readout system comprising:
an image recording medium, on which image information has been recorded; and
a scanning exposure apparatus for performing scanning exposure, employing linear light beams as readout light, on the image recording medium, in a scanning direction perpendicular to the longitudinal direction of the linear light beams; wherein:
the scanning exposure apparatus comprises:
a panel light source comprising:
at least one planar light transmissive electrode;
a plurality of linear electrodes, which are arranged in a first direction; and
an EL layer, provided between the light transmissive electrode and the linear electrodes; and
an exposure control means for causing electric current to flow through the linear electrodes in a sequential manner, thereby causing electric current to flow in the EL layer provided between the light transmissive planar electrode and the linear electrodes, to cause sequential emission of the linear light beams, wherein
the linear electrodes are formed by thin films having a sheet resistance ra, widths wa, and which are arranged at a pitch P;
the at least one light transmissive electrode is formed by a plurality of rectangular thin films having a sheet resistance rc, which are arranged in the first direction at substantially equidistant gaps having a width wi; and
the width wc of the light transmissive electrode satisfies the equation: wc≧n·P−wi, wherein n is the maximum integer that satisfies the equation:
$$n < \frac{wa \cdot rc}{ra \cdot P}.$$

5. An image information readout system as defined in claim 4, wherein:
the image recording medium is an electrostatic recording medium that records image information as an electrostatic latent image, and generates electric current corresponding to the electrostatic latent image when subjected to scanning exposure by the readout light.

6. An image information readout system as defined in claim 4, wherein:
the image recording medium is a stimulable phosphor recording medium that accumulatively records image information, and emits stimulated phosphorescence corresponding to the image information when subjected to scanning exposure by the readout light.

7. A line light source, comprising:
linear electrodes;
opposing electrodes corresponding to the linear electrodes; and
an EL layer provided between the linear electrodes and the opposing electrodes; wherein:
either one of the linear electrodes and the opposing electrodes are light transmissive;
linear light beams are emitted by applying a drive voltage to a first end of the linear electrodes, causing electric current to flow between the linear electrodes and the opposing electrodes through the EL layer;
a voltage different from the drive voltage is applied to the opposing electrodes at a portion facing a second end of the linear electrodes, to which the drive voltage is not applied; and
the ratio of the resistance between the two ends of the linear electrodes, with respect to the resistance between the portions of the opposing electrodes corresponding to the two ends of the linear electrodes is 0.5 or greater and 2 or less.

8. A line light source as defined in claim 7, wherein:
the ratio is 0.9 or greater and 1.1 or less.

9. A line light source as defined in claim 8, wherein:
the ratio is 1.

10. A line light source as defined in claim 9, wherein:
if the linear electrodes are formed by thin films having a sheet resistance ra, widths wa, and lengths L, the resistance of the linear electrodes is expressed as
$$\frac{ra \cdot L}{wa}; \text{ and}$$

if the opposing electrodes are formed as rectangles by thin films having a sheet resistance rc, widths wc, and lengths L, the resistance of the opposing electrodes is expressed as
$$\frac{rc \cdot L}{wc}.$$

11. A line light source as defined in claim 8, wherein:
if the linear electrodes are formed by thin films having a sheet resistance ra, widths wa, and lengths L, the resistance of the linear electrodes is expressed as
$$\frac{ra \cdot L}{wa}; \text{ and}$$

if the opposing electrodes are formed as rectangles by thin films having a sheet resistance rc, widths wc, and lengths L, the resistance of the opposing electrodes is expressed as
$$\frac{rc \cdot L}{wc}.$$

12. A line light source as defined in claim 7, wherein:
if the linear electrodes are formed by thin films having a sheet resistance ra, widths wa, and lengths L, the resistance of the linear electrodes is expressed as
$$\frac{ra \cdot L}{wa}; \text{ and}$$

if the opposing electrodes are formed as rectangles by thin films having a sheet resistance rc, widths wc, and lengths L, the resistance of the opposing electrodes is expressed as $$\frac{rc \cdot L}{wc}.$$

13. An image information readout system comprising:
an image recording medium, on which image information has been recorded;
an exposure head, in which a plurality of line light sources for emitting readout light are arranged; and
a scanning exposure control portion for causing the readout light to be emitted by the line light sources at different timings, during readout of the image information; wherein:
the line light source comprises:
 linear electrodes;
 opposing electrodes corresponding to the linear electrodes; and
an EL layer provided between the linear electrodes and the opposing electrodes;
either one of the linear electrodes and the opposing electrodes are light transmissive;
linear light beams are emitted by applying a drive voltage to a first end of the linear electrodes, causing electric current to flow between the linear electrodes and the opposing electrodes through the EL layer;
a voltage different from the drive voltage is applied to the opposing electrodes at a portion facing a second end of the linear electrodes, to which the drive voltage is not applied; and
the ratio of the resistance between the two ends of the linear electrodes, with respect to the resistance between the portions of the opposing electrodes corresponding to the two ends of the linear electrodes is 0.5 or greater and 2 or less.

14. An image readout system as defined in claim 13, wherein:
the image recording medium is an electrostatic recording medium that records image information as an electrostatic latent image, and generates electric current corresponding to the electrostatic latent image when subjected to scanning exposure by the readout light.

15. An image information readout system as defined in claim 13, wherein:
the image recording medium is a stimulable phosphor recording medium that accumulatively records image information, and emits stimulated phosphorescence corresponding to the image information when subjected to scanning exposure by the readout light.

* * * * *